(12) United States Patent
Fahy

(10) Patent No.: US 6,203,990 B1
(45) Date of Patent: Mar. 20, 2001

(54) METHOD AND SYSTEM FOR PATTERN ANALYSIS, SUCH AS FOR ANALYZING OLIGONUCLEOTIDE PRIMER EXTENSION ASSAY PRODUCTS

(75) Inventor: Eoin David Fahy, San Diego, CA (US)

(73) Assignee: MitoKor, San Diego, CA (US)

(*) Notice: Subject to any disclaimer, the term of this patent is extended or adjusted under 35 U.S.C. 154(b) by 0 days.

(21) Appl. No.: 09/289,793

(22) Filed: Apr. 9, 1999

Related U.S. Application Data

(60) Provisional application No. 60/107,360, filed on Nov. 6, 1998.

(51) Int. Cl.[7] .............................. C02F 1/40; C25B 11/00; C12Q 1/68; C12Q 1/70
(52) U.S. Cl. ................................. 435/6; 435/5; 422/64; 204/612; 204/606
(58) Field of Search ............................. 422/64; 23/230; 435/6, 5; 204/612, 606

(56) References Cited

U.S. PATENT DOCUMENTS

| | | |
|---|---|---|
| 5,061,067 | 10/1991 | Yamamoto et al. . |
| 5,205,917 | 4/1993 | Klock, Jr. . |
| 5,400,249 * | 3/1995 | Soll et al. .................. 364/413.13 |
| 5,693,463 | 12/1997 | Edwards et al. . |

FOREIGN PATENT DOCUMENTS

WO 90/09455  8/1990  (WO).

OTHER PUBLICATIONS

Manabe, T. et al, "Studies on the Procedure for the Construction of Cellular Protein Databases Employing Micro 2–Delectrophoresis: An HL–60 Protein Database", *Electrophoresis*, vol. 16, No.3, Mar. 1995 p 406–422.*

Microsoft Corporation, *Microsoft Excel User's Guide I, & II*, 1992–1993, pp 175–176, 328–337, pp. 121–122, 127–129.*

Umenishi, F, et al, "Mitoconidrial DNA Polymorphism in Jindo Dogs",*Journal of Veterinary Medicine* (Apr. 1993), 55(2) p313–7.*

Gong, Jianping, et al., "A Selective Procedure for DNA Extraction From Apoptotic Cells Applicable for Gel Electrolysis and Flow Cytometry", *Analytical Biochemistry*, vol. 218, No. 2, May 1, 1994 pp 314–319.*

Appel, R.D, et al, "Federated 2–D Electrophoresis Database: A Simple Means of Publishing Two–Dimensional Electrophoresis Data", *Electrophorosis*, Mar. 1996, vol. 17 p 540–546.

Ashley, L., "DNA Sequencing: From Experimental Methods to Bioinformatics," Springer–Verlag/Bios Scientific Publishers, UK XP002133800, Section 10.3, Paragraph 2, pp. 101–110, 1997.

Anderson et al., "Sequence and Organization of the Human Mitochondrial Genome," *Nature* 290:457–465, 1981.

Fahy et al., "Multiplex Fluorescence–Based Primer Extension Method for Quantitative Mutation Analysis of Mitochondrial DNA and Its Diagnostic Application for Alzheimer's Disease," *Nucleic Acids Research* 25(15):3102–3109, 1997.

Ghosh et al., "Longitudinal Study of a Heteroplasmic 3460 Leber Hereditary Optic Neuropathy Family by Multiplexed Primer–Extension Analysis and Nucleotide Sequencing," *Am. J. Hum. Genet.* 58:325–334, 1996.

Ikonen et al., "Quantitative Determination of Rare mRNA Species by PCR and Solid–Phase Minisequencing," *PCR Methods and Applications* 1:234–240, 1992.

Ikonen et al., "Spectrum of Mutations in Aspartylglucosaminuria," *Proc. Natl. Acad. Sci. USA* 88:11222–11226, 1991.

Juvonen et al., "Quantification of Point Mutations Associated with Leber Hereditary Optic Neuroretinopathy by Solid–Phase Minisequencing," *Hum. Genet. 93*: 16–20, 1994.

Krook et al., "Rapid and Simultaneous Detection of Multiple Mutations by Pooled and Multiplex Single Nucleotide Primer Extension: Applicaiton to the Study of Insulin–Responsive Glucose Transporter and Insulin Receptor Mutations in Non–Insulin–Dependent Diabetes,"*Human Molecular Genetics* 1(6):391–395, 1992.

Kuppuswamy et al., "Single Nucleotide Primer Extension to Detect Genetic Diseases: Experimental Application to Hemophilia B (factor IX) and Cystic Fibrosis Genes," *Proc. Natl. Acad. Sci. USA* 88:1143–1147, 1991.

Nikiforov et al., "Genetic Bit Analysis: a Solid Phase Method for Typing Single Nucleotide Polymorphisms, "*Nucleic Acids Research* 22(20):4167–4175, 1994.

Syvänen et al., "A Primer–Guided Nucleotide Incorporation Assay in the Genotyping of Apolipoprotein E," *Genomics* 8:684–692, 1990.

Backer JM et al, "Interaction of Benzo(a)pyrene and its dihydrodiol–epoxide derivative with nuclear and mitochondrial DNA in C3H10T1/2 cell cultures", Cancer Research, vol. 42, Jul. 1982, pp. 2764–2769.*

Singh G et al, "Evidence for lack of mitochondrial DNA repair following cis dichlorodiammineplatinum treatment", Cancer Chemother. Pharmacol., (1990), 26(2), pp. 97–100.*

* cited by examiner

Primary Examiner—John S. Brusca
Assistant Examiner—Stephen Siu
(74) Attorney, Agent, or Firm—Michael J. Donohue; Seed IP Law Group PLLC

(57) ABSTRACT

A system and corresponding method analyzes data for patterns, such as data produced from DNA sequencers. An ASCII text file, generated by DNA sequencer software, is used as the input source for the pattern analysis software program. This text file contains peak intensity data, identified by gel-lane and mobility, for bands corresponding to 2 sequences of differing length. The software uses gel-mobility values of control DNA samples to identify bands of interest from test samples in the dataset. Spurious data point or artifacts are filtered out in this selection process. The selected data is then imported to a second software program that performs algorithms such as linear progression and curve fitting.

35 Claims, 15 Drawing Sheets

MIN. SIZE PEAK HEIGHT PEAK AREA SCAN NUMBER

| | A | B | C | D | F | I | J | K | L |
|---|---|---|---|---|---|---|---|---|---|
| 1 | Study # 123 | | | | | | | | |
| 2 | | PE Data | | | | Sequencer | 60 | | ~1402 |
| 3 | | | | | | | | | |
| 4 | | Linear Regression Data | | | | Loaded by: | M2 | | ~1404 |
| 5 | | | | | | | | | |
| 6 | Patient ID | | MitoLoad | | | Date: | 8/19/98 | | |
| 7 | | | | | | | Gel Lane | | |
| 8 | 1 | | 1.2 | | | | 9 | | |
| 9 | 2 | | 0.0 | | | | 10 | | |
| 10 | 3 | | 0.0 | | | | 11 | | |
| 11 | 4 | | 9.3 | | | | 12 | | |
| 12 | 5 | | 11.5 | | | | 13 | | |
| 13 | 6 | | 4.8 | | | | 14 | | |
| 14 | 7 | | 5.9 | | | | 15 | | |
| 15 | 8 | | 4.6 | | | | 16 | | |
| 16 | 9 | | 2.3 | | | | 17 | | |
| 17 | 10 | | 11.9 | | | | 18 | | |
| 18 | 11 | | 10.0 | | | | 19 | | |
| 19 | 12 | | 9.7 | | | | 20 | | |
| 20 | 13 | | 10.9 | | | | 21 | | |
| 21 | 14 | | 12.0 | | | | 22 | | |
| 22 | 15 | | 6.8 | | | | 23 | | |

*Fig. 14*

METHOD AND SYSTEM FOR PATTERN ANALYSIS, SUCH AS FOR ANALYZING OLIGONUCLEOTIDE PRIMER EXTENSION ASSAY PRODUCTS

CROSS-REFERENCE TO RELATED APPLICATION

This application claims the benefit of U.S. Provisional Patent Application No. 60/107,360, filed Nov. 6, 1998, currently pending, incorporated herein by reference.

TECHNICAL FIELD

The invention relates generally to analyzing multiple samples, including apparatus and related methods for inputting and analyzing data derived from oligonucleotide assays of biological samples.

BACKGROUND OF THE INVENTION

Inherited and acquired genetic disorders account for a large percentage of today's health care costs. Early diagnosis of such diseases is not only important for successful treatment, but also contributes to lower overall costs to the public. Lower costs result, for example, because many diseases can be averted or even treated before patients present chronic symptoms, which require expensive procedures and/or hospitalization. A "genetic disorder" refers to any disease that has as an underlying basis an abnormality in one or more genes of an afflicted individual. Detecting a genetic disorder can require extensive information processing. A brief background is provided here describing basic molecular biology as it relates to sources of data significant in diagnosing genetic disorders.

It is well established that a long, polymeric molecule known as DNA (deoxyribonucleic acid) is the genetic material that stores and encodes biological information, and through which inherited traits are passed from one generation to the next. An individual whose DNA contains no irregularities in a particular gene responsible for a given trait may be said to possess a wildtype genetic complement (genotype) for that gene, while the presence of irregularities known as mutations in the DNA for the gene indicates a mutated or mutant genotype.

DNA is a linear polymer formed from four types of subunits called nucleotides, each consisting of a nitrogen-containing carbon ring structure (the nucleotide "base") linked to a 5-carbon sugar attached to a phosphate group (see, e.g., Watson, Hopkins, Roberts, Steitz & Weiner, *The Molecular Biology of the Gene*, 4th ed., 1987, Benjamin/Cummings Publishing, Menlo Park, Calif.). The four subunits, which differ in the particular base structure present, are adenine, guanine, cytosine and thymine (abbreviated, respectively, as A, G, C and T). A segment or region of a DNA molecule may encode a particular protein by specifying the production of a ribonucleic acid (RNA) intermediate molecule known as a messenger RNA (mRNA), which directs the synthesis of the particular protein. Other regions of a DNA molecule may encode other types of functionally important RNA, or may operate by a variety of mechanisms that do not involve the encoding of RNA.

A DNA molecule generally occurs as a double helix formed by one pair of linear strands oriented so that the bases in each strand structurally align and form hydrogen bonds in "complementary" fashion, such that A pairs with T, and G pairs with C. This reversible assembly of double stranded DNA is known as base-pairing. Thus, the sequence of nucleotide bases on one strand dictates what the sequence of bases on the complementary strand must be, in order for the double stranded or "duplex" DNA helix to form. The double helix is a dynamic structure, and transient disruption of complementary base pairing accompanies processes such as expression of genes to produce proteins.

Proteins, which are biological molecules of enormous importance, include major structural materials of the animal body, enzymes that catalyze numerous biochemical reactions, many hormones, and other biologically significant structural and functional components. Proteins are assembled from one or more large, linear polymeric chains of covalently linked building blocks known as amino acids. The chemical bonds linking amino acids together are called peptide bonds, hence proteins may also be referred to as peptides or polypeptides. There are 20 amino acids that may be strung together in assorted lengths and orders to generate the hundreds of thousands of naturally occurring proteins having distinct amino acid sequences.

DNA molecules do not directly participate in synthesizing proteins. Instead, DNA acts as a permanent blueprint of genetic information within a cell. DNA exists as extraordinarily long strands in the chromosomes present in the cell nucleus, and is also present in the form of a much smaller, circular DNA molecule in subcellular structures responsible for cellular energy production, known as mitochondria. The region of DNA that codes for a sequence of a single polypeptide is called a gene, which must first be copied into an RNA molecule before the polypeptide (i.e., a protein) can be produced.

The structure of RNA closely resembles that of DNA, except the 5-carbon sugar (ribose) replaces the deoxyribose of DNA, and instead of the base thymine, RNA contains the structurally related nucleotide base uracil (U). Synthesizing an RNA copy of a portion of DNA is called transcription, wherein a region of double stranded DNA transiently separates into single strands, and RNA nucleotides are incorporated, according to nucleotide base-pairing in a manner complementary to the DNA template. This mechanism permits assembly of RNA nucleotides into a linear polymer in a sequence governed by the DNA template coding sequence. The resulting mRNA is translated into protein by cellular machinery that reads the mRNA as a series of three-nucleotide "words" known as codons. Each codon specifies the addition of a particular amino acid to a protein (polypeptide) chain, such that the linear order of codons in the mRNA predicts the linear order of amino acids in the protein. Additionally, certain codons known as stop codons do not specify any amino acid, but instead provide a signal to terminate the synthesis of a polypeptide chain.

Occasionally, a natural or non-natural influence may chemically change a specific location in a DNA sequence in a process called mutation, leading to a change in the nucleotide base situated at a particular position in the DNA molecule. This mutation, which may be manifested as a deletion (removal of one or more nucleotides from the DNA chain), an insertion (addition of one or more nucleotides to the DNA chain) or a substitution (switch from one base to another with no net change in chain length, e.g., a C is replaced with a T), will lead to a corresponding change in the RNA transcribed from the DNA. As such, a mutation may result in codon changes that cause a significantly altered protein amino acid sequence to be produced. Thus, it is apparent that heritable alterations in a DNA nucleotide sequence (i.e., a gene) can result in dramatically abnormal gene products (e.g., proteins). Similarly, mutations in DNA regions that do not encode mRNA (for translation into proteins), but that do encode other functional RNAs, or in DNA regions that function without being transcribed into RNA, are nevertheless passed on to progeny. In any case, detecting a genetic disorder at the level of a DNA mutation may be highly advantageous.

A wide variety of methods in molecular biology are known for detecting mutations in nucleic acids such as DNA or RNA. These include, for example, restriction fragment length polymorphism analysis, direct nucleic acid sequencing, polymerase chain reaction, oligonucleotide primer extension assay, ligase chain reaction, and other techniques based on detecting a signal derived from specific base-pairing between an oligonucleotide probe and a complementary region of a nucleic acid target. Such specific base-pairing or duplex formation is known as hybridization, and those familiar with the art are readily able to devise suitable hybridization conditions that permit detecting even a single nucleotide mismatch (e.g., a mutation) between a probe and its target (see, e.g., Ausubel et al., *Current Protocols in Molecular Biology,* Greene Publishing, 1987; Sambrook et al., *Molecular Cloning: A Laboratory Manual,* Cold Spring Harbor Press, 1989).

Recent technological advances in molecular biology and related arts permit rapid and sensitive detection of nucleic acid sequence information (including point mutations) in increasingly large numbers of samples, where smaller quantities of samples are required. These advances provide high throughput screening formats capable of generating large volumes of data. Such increases in the ability to generate data, however, have not been matched by suitable methods for processing and analyzing such data.

For example, most nucleic acid detection methods, including methods for detecting point mutations, rely on quantifying a reporter signal generated directly by a labeled molecule incorporated into the assay components, such as a fluorophore, a chromophore, a radionuclide or a detectable enzyme, or indirectly by quantification of an image generated by such reporter signals using image analysis routines (see, e.g., www.dnapro.com). Further, quantitatively analyzing such reporter signals typically requires labor-intensive and often tedious data manipulation, often involving serial routines whereby organizing and calculating various data sets must be performed manually. Given the dramatic increase in the ability to generate genetic data, there is a need for improved devices and methods capable of flexibly extracting, calibrating, formatting and manipulating raw data derived from multiparameter analysis of nucleic acid samples for detecting mutations.

SUMMARY OF THE INVENTION

Aspects of the invention include a method for generating information based on biological samples. The method includes the steps of: receiving a set of data produced from testing a set of biological samples, wherein the biological samples include test samples and at least one control sample related to at least some of the test samples by space, time or frequency, wherein the set of data includes first and second values and a quantitative value for each test sample; identifying first or second values corresponding to the control sample in the set of data; identifying first or second values for at least some of the test samples in the set of data based on the identified first or second values of the control sample and the spatial, temporal or frequency relationship between the control sample and the at least some of the test samples; filtering the quantitative values for the at least some of the test samples in the set of data based on the identified first or second values; and analyzing the filtered quantitative values to produce a report of the analyzed quantitative values.

Additional aspects of the invention include a computer-readable medium for storing instructions for a computer, and a biological assay system that includes a biological assay device and a computer. Numerous additional aspects of the invention are identified in the following detailed description, together with the figures.

BRIEF DESCRIPTION OF THE DRAWINGS

In the drawings, like reference numbers identify similar elements or steps. For ease in identifying the discussion of any particular element or step, the most significant digit in a reference number refers to the Figure number in which that element is first introduced (e.g., element 204 is first introduced and discussed with respect to FIG. 2).

FIG. 4 is a table of raw data produced by a DNA sequencer, such as that shown in FIG. 1, based on test samples, such as the gel plate of FIG. 2.

FIG. 10 is a display screen showing filtration of the input data of FIG. 7.

FIG. 13 is a display screen showing analyzed output data produced from the input data of FIG. 7.

FIG. 14 is a display screen showing a summary of output data produced from the data of FIG. 13.

DETAILED DESCRIPTION OF THE INVENTION

Figure 1:
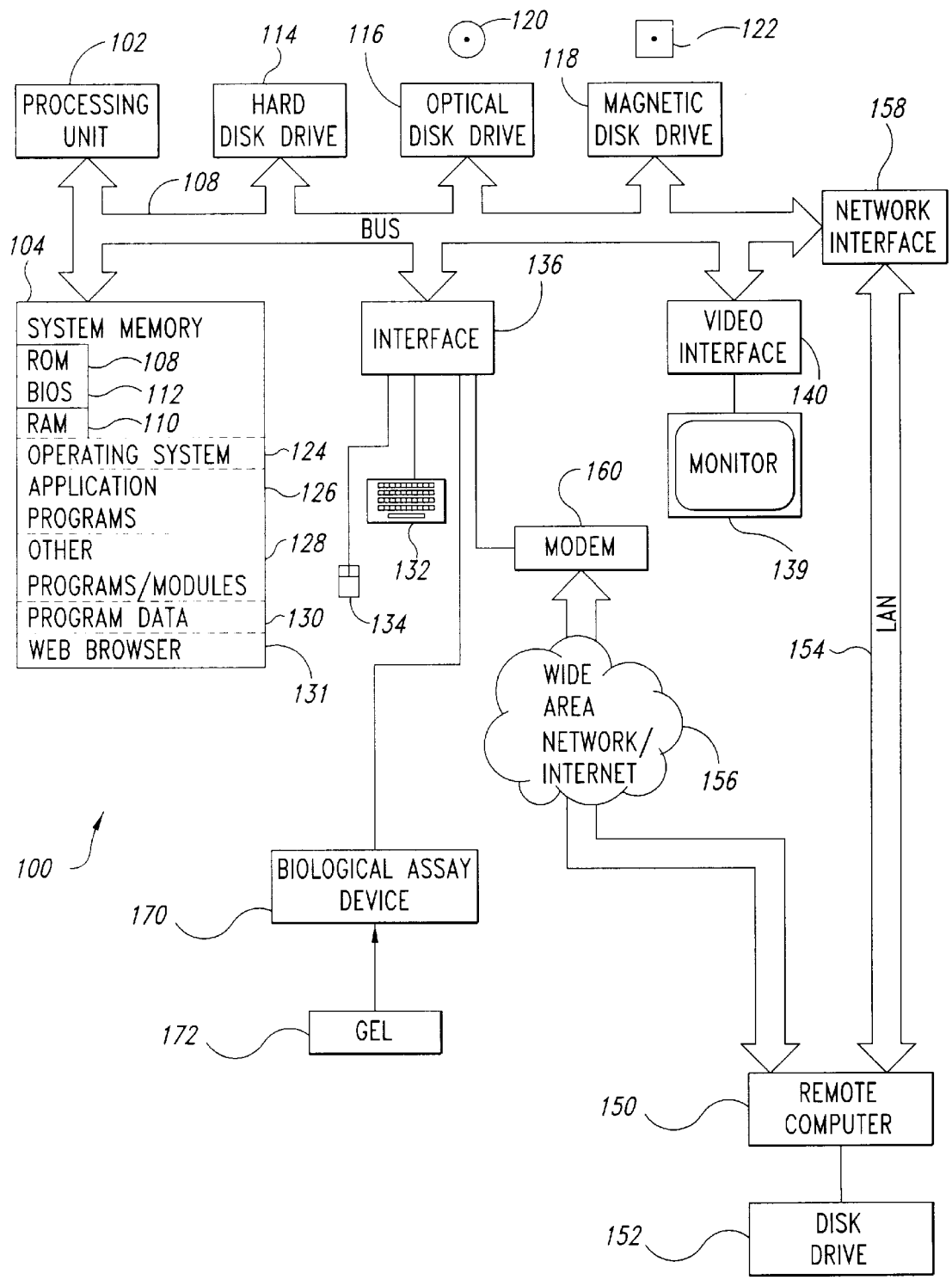
FIG. 1 is a block diagram of a computing system suitable for employing aspects of the invention to analyze assay data.

A data analysis system, and in particular, an apparatus and related method for analyzing data produced from, for example, biological assay tools, is described in detail herein. In the following description, numerous specific details are provided, such as specific input data, filtering techniques, analysis methods, etc., to provide a thorough understanding of embodiments of the invention. One skilled in the relevant art, however, will recognize that the invention can be practiced without one or more of these specific details, or with other input data, filtering techniques, analysis methods, etc. In other instances, well-known structures or operations are not shown, or not described in detail, to avoid obscuring aspects of the invention.

The methods of the present invention may be useful for processing and/or analyzing data, including for pattern analysis such as analysis of oligonucleotide primer extension assay products as described below, but need not be so limited. The methods may also be useful for processing and/or analyzing data generated using any three-parameter system wherein the parameters may include (i) a sample identifier; (ii) a positional sample indicator determined in a gel or other device capable of spatial, temporal or spatiotemporal discrimination of a sample, for example by way of illustration and not limitation, sample migration distance in gel electrophoresis, for example as may be used in DNA and/or protein fragment analysis (e.g., "fingerprinting") such as DNA restriction fragment length polymorphism (RFLP) analysis; sample retention time and/or elution time in gas, liquid or gas/liquid chromatography; sample retention time and/or elution time in capillary electrophoresis or isotachophoresis; sample position identification by particle analysis or image analysis, including for example, particle flow analysis such as flow cytometry or flow immunocytofluorimetry; or other sample positional indicators; and (iii) a detectable sample signal strength, such as may be determined using a biological assay device as described herein, or any device capable of quantifying a signal, which may be expressed, for example, as signal amplitude, peak height, signal intensity or the like. A signal may be detected, for example, by means such as spectrophotometric, spectroscopic including mass spectrometric, colorimetric, fluorimetric, radiometric, electrochemical including pulsed amperometric means, or by any other suitable signal detection means appropriate for a particular sample and with which those having ordinary skill in the art will be familiar.

Biological samples containing nucleic acid, and in certain embodiments containing exmtDNA and mtDNA as described below, may comprise any tissue or cell preparation in which nucleic acids (e.g., exmtDNA and mtDNA) may be present. Compositions and methods useful for detecting exmtDNA and mtDNA are provided, for example, in U.S. application Ser. Nos. 09/098,079 and 09/097,889. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like. In certain embodiments of the invention, the subject or biological source may be suspected of having or being at risk for having a disease associated with altered mitochondrial function, and in certain embodiments of the invention, the subject or biological source may be known to be free of a risk or presence of such a disease.

In certain other preferred embodiments it may be desirable to determine whether a subject or biological source falls within clinical parameters indicative of Alzheimer's disease (AD). Signs and symptoms of AD accepted by those skilled in the art may be used to so designate a subject or biological source, for example clinical signs referred to in McKhann et al. (*Neurology* 34:939, 1984, National Institute of Neurology, Communicative Disorders and Stroke and Alzheimer's Disease and Related Disorders Association Criteria of Probable AD, NINCDS-ADRDA) and references cited therein, or other means known in the art for diagnosing AD.

In other preferred embodiments, it may be desirable to determine whether a subject or biological source falls within clinical parameters indicative of diseases other than AD. Diseases and disorders to which the invention may be applied include, without limitation, mitochondria associated diseases, including but not limited to neurodegenerative disorders such as Parkinson's disease (PD); auto-immune diseases; diabetes mellitus, including Type I and Type II; MELAS, MERFF, arthritis, NARP (Neuropathy; Ataxia; Retinitis Pigmentosa); MNGIE (Myopathy and external ophthalmoplegia; Neuropathy; Gastro-Intestinal; Encephalopathy), LHON (Leber's; Hereditary; Optic; Neuropathy), Kearns-Sayre disease; Pearson's Syndrome; PEO (Progressive External Ophthalmoplegia); congenital muscular dystrophy with mitochondrial structural abnormalities; Wolfram syndrome (DIDMOAD; Diabetes Insipidus, Diabetes Mellitus, Optic Atrophy, Deafness), Leigh's Syndrome, fatal infantile myopathy with severe mtDNA depletion, benign "later-onset" myopathy with moderate reduction in mtDNA; dystonia; schizophrenia; mitochondrial encephalopathy, lactic acidosis, and stroke (MELAS); mitochondrial diabetes and deafness (MIDD); myoclonic epilepsy ragged red fiber syndrome (MERFF); and hyperproliferative disorders, such as cancer, tumors and psoriasis.

In one embodiment of the invention, a biological sample containing mtDNA and exmtDNA may comprise a crude buffy coat fraction of whole blood, which is known in the art to comprise further a particulate fraction of whole blood enriched in white blood cells and platelets and substantially depleted of erythrocytes. Those familiar with the art will know how to prepare such a buffy coat fraction, which may be prepared by differential density sedimentation of blood components under defined conditions, including the use of density dependent separation media, or by other methods.

In another embodiment of the invention, the amount of exmtDNA and mtDNA in a biological sample may be quantified by first heating the sample in water to lyse cells contained therein, and then extracting cellular DNA from the lysed cells using an aqueous DNA extraction procedure. "Heating" may involve treating the cells for various times, typically 1–120 minutes, at a high temperature of at least 80° C., preferably at least 90° C., more preferably at least 95° C. and most preferably in a boiling water bath. Based on the compositions and methods disclosed herein, the ordinarily skilled artisan will be able to readily determine optimal times and temperatures for heating samples to practice the invention without undue experimentation. As used herein, an "aqueous DNA extraction" method refers to preparing DNA from such a boiled cell lysate without subjecting the lysate to sodium dodecylsulfate(SDS)/proteinase K treatments and/or without fractionating the lysate using a phenol-chloforn two-phase separation extraction step. Those skilled in the art will be familiar with various standard procedures for preparing and handling DNA without the use of SDS/ proteinase K and/or phenol-chloroform.

According to certain embodiments of the invention, the particular cell type or tissue type from which a biological sample is obtained may influence qualitative or quantitative aspects of the exmtDNA and/or mtDNA contained therein relative to exmtDNA and/or mtDNA obtained from distinct cell or tissue types of a common biological source. As described above, some diseases associated with altered mitochondrial function may manifest themselves in particular cell or tissue types. For example, AD is primarily a neurodegenerative disease that particularly effects changes in the central nervous system (CNS). It is therefore within the contemplation of the invention to quantify exmtDNA and mtDNA in biological samples from different cell or tissue types as may render the advantages of the invention most useful for a particular disease associated with altered mitochondrial function, and the relevant cell or tissue types will be known to those familiar with such diseases.

The present invention provides compositions and methods useful in pharmacogenomics, for the classification and/or stratification of a subject or a patient population, for instance correlating one or more traits in a subject with indicators of the responsiveness to, or efficacy of, a particular therapeutic treatment. In certain embodiments of the invention, a ratio, r, is determined, which may be useful for pharmacogenomic purposes, for example to stratify patient populations according to the suitability of particular therapeutic agents for use in such populations. The ratio r is the ratio of the amount of exmtDNA in a biological sample relative to the sum of the amount of exmtDNA plus mtDNA in the sample. As expressed quantitatively, the ratio r may be calculated using the formula:

$$r = x/(x+y)$$

wherein x is the amount of exmtDNA in a sample, and y is the amount of mtDNA in the sample.

In certain embodiments, measuring r in a biological sample from a subject is combined with identifying the subject's apolipoprotein E (APOE) genotype to determine the risk for, or presence of, Alzheimer's disease (AD) in the subject. The apolipoprotein E type 4 allele (APOE-$\epsilon$4) allele is a genetic susceptibility factor for sporadic AD and confers a two fold risk for AD (Corder et al., *Science* 261:921, 1993; see also "National Institute on Aging/Alzheimer's Association Working Group Consensus Statement," *Lancet* 347:1091, 1996, and references cited therein, all of which are hereby incorporated by reference in their entireties). Accordingly, in an embodiment of the invention, the method for determining the risk for or presence of AD in a subject by comparing r values will further comprise determining the APOE genotype of the subject suspected of being at risk for AD. By using the combination of the methods for determining r, as disclosed herein, and methods known in the art for determining APOE genotype, an enhanced ability to detect the relative risk for AD is provided by the instant invention along with other related advantages. Similarly, where APOE genotype and risk for AD are correlated, the present invention provides advantageous methods for identifying agents suitable for treating AD where such agents affect r in a biological source.

As described herein, determining r may be used to stratify an AD patient population. Accordingly, in another embodiment of the invention, determining r in a biological sample from an AD subject may provide a useful correlative indicator for that subject. An AD subject so classified on the basis of an r value may then be monitored using AD clinical parameters referred to above, such that correlating between an r value and any particular clinical score used to evaluate AD may be monitored. For example, stratifying an AD patient population according to r values may provide a useful marker with which to correlate the efficacy of any candidate therapeutic agent being used in AD subjects. In a further embodiment of the invention, determining r in concert with determination of an AD subject's APOE genotype may also be useful. For example, r may be determined according to the present invention using an oligonucleotide primer extension assay that specifically quantifies (i) mtDNA encoding codon 22 of the cytochrome c oxidase subunit 2 (COX2) gene, and (ii) exmtDNA highly homologous to the region of COX2 mtDNA containing codon 22 but distinguishable by a single nucleotide substitution in that codon. As another example, the present invention may be useful in determining the genotype of human APOE alleles on chromosome 19, which have been implicated in AD. As another example, the present invention may be used to quantify the heteroplasmy of a mtDNA point mutation responsible for Leber's hereditary optic neuropathy (LHON, see, e.g., Ghosh et al., *Am. J. Hum. Genet.* 58:325, 1996). These and related advantages will be appreciated by those familiar with the art.

The present invention is particularly useful for manipulating and analyzing data generated in detecting single nucleotide base mutations or "point" mutations, although the invention need not be so limited. As noted above, mutations may occur in DNA present in the cell nucleus, for example as chromosomal DNA or as extramitochondrial DNA (exmtDNA) highly homologous to mtDNA but found outside of mitochondria, and may also be present in mitochondrial DNA (mtDNA). Accordingly, certain embodiments may be particularly useful for identifying and quantifying heteroplasmy, that is, the presence of two distinct forms (or "alleles") of a mitochondrial gene, where such mitochondrial alleles (e.g., mutant vs. wildtype, Anderson et al., *Nature* 290:456, 1981) are detected by detecting particular point mutations.

In certain other embodiments, the subject invention method may be directed to compositions and methods for analyzing the relative proportions in a sample of mitochondrial DNA (mtDNA) and extramitochondrial DNA (exmtDNA, e.g., nuclear DNA sequences having high homology to mtDNA), including those set forth in U.S. application Ser. Nos. 09/098,079 and 09/097,889.

Analyzing point mutations in DNA may be performed using any suitable technique known in the art, for example, using variants of the polymerase chain reaction (PCR) (see, e.g., Gibbs et al., *Nucl. Acids. Res.* 17:2437–2448, 1989; Newton et al., *Nucl. Acids. Res.* 17:2503–2516, 1989). Point mutations may also be detected by using enzyme mediated oligonucleotide ligation methods, for example, wherein mutations are detected when oligonucleotide sequences annealed immediately adjacent to each other on a target DNA or RNA molecule are covalently attached only if oligonucleotides are correctly base-paired. (Grossman et al., *Nucleic Acids Research* 22:4527–4534, 1994). Single base mutations in target nucleic acids may also be detected by differential hybridization techniques using allele-specific oligonucleotide (ASO) probes (e.g., Saiki et al., *Proc. Natl. Acad. Sci. USA* 86:6230–6234, 1989). Other suitable techniques include, for example, those disclosed in U.S. Pat. No. 5,760,205 and references cited therein, and in Botstein et al. (*Am. J. Hum. Gen.* 32:314, 1980), which are incorporated herein by reference in their entireties.

In certain embodiments of the invention, single nucleotide primer-guided extension assays may be used for detecting and quantifying point mutations (see, e.g., Kuppuswamy et al., *Proc. Natl. Acad. Sci. USA,* 88:1143–1147, 1991; Syvanen et al., *Genomics* 8:684–692, 1990; Juvonen et al., *Human Genetics* 93:1620, 1994; Ikonen et al., *PCR Meth. Applications* 1:234–240, 1992; Ikonen et al., *Proc. Natl. Acad. Sci. USA* 88:11222–11226, 1991; Nikiforov et al.,

*Nucleic Acids Research* 22:4167–4175, 1994). The single nucleotide primer extension reaction approach may be modified in certain embodiments to provide "multiplexing", or simultaneous detection of multiple mutations (see, e.g., Krook et al., *Human Molecular Genetics* 1:391–395, 1992). Multiplexing may be achieved by using multiple primers having different lengths in a reaction containing mixed (e.g., mtDNA and exmtDNA; or optionally, e.g., wildtype and mutant) templates, and/or by monitoring the wild-type and mutant nucleotide at each mutation site in two separate single nucleotide incorporation reactions. The reaction mixtures are resolved by gel electrophoresis and the identity of the nucleotide in the mutation site is determined by the presence of a correct size band in the wild-type or mutant nucleotide lanes. Use of the primer extension technique, including multiplexed detection of (i) more than one target (e.g., template) sequence, or of (ii) the presence of specific nucleotides in different target sequences using differentiable primers for nucleic acid detection and mutational analysis, is also described in PCT WO 90/09455.

A particularly useful method is the primer extension assay disclosed by Fahy et al. (*Nucl. Acids Res.* 25:3102, 1997) and by Ghosh et al. (*Am. J. Hum. Genet.* 58:325, 1996), both of which are incorporated herein by reference in their entireties.

Examples of other useful techniques for determining the amount of specific nucleic acid target sequences (e.g., mutant vs. wildtype, mtDNA vs. exmtDNA) present in a sample based on specific hybridization of a primer to the target sequence include specific amplification of target nucleic acid sequences and quantification of amplification products, including but not limited to polymerase chain reaction (PCR, Gibbs et al., *Nucl. Ac. Res.* 17:2437, 1989), transcriptional amplification systems (e.g., Kwoh et al., 1989 *Proc. Nat. Acad. Sci.* 86:1173); strand displacement amplification (e.g., Walker et al., *Nucl. Ac. Res.* 20:1691, 1992; Walker et al., *Proc. Nat. Acad. Sci.* 89:392, 1992) and self-sustained sequence replication (3SR, see, e.g., Ghosh et al, in Molecular Methods for Virus Detection, 1995 Academic Press, NY, pp. 287–314; Guatelli et al., *Proc. Nat. Acad. Sci.* 87:1874, 1990), the cited references for which are incorporated herein by reference in their entireties. Other useful techniques include, for example, ligase chain reaction (e.g., Barany, *Proc. Nat. Acad. Sci.* 88:189, 1991), single stranded conformational polymorphism analysis, Q-beta replicase assay (Cahill et al., *Clin. Chem.* 37:1482, 1991; Lizardi et al., *Biotechnol.* 6:1197, 1988; Fox et al., *J. Clin. Lab. Analysis* 3:378, 1989), restriction fragment length polymorphism (RFLP, Botstein et al., *Am. J. Hum. Gen.* 32:314, 1980) analysis and cycled probe technology (e.g., Cloney et al., *Clin. Chem.* 40:656, 1994), as well as other suitable methods that will be known to those familiar with the art.

In one embodiment of the invention, primer extension is used to quantify exmtDNA and mtDNA present in a biological sample (Ghosh et al., *Am. J. Hum. Genet.* 58:325, 1996; see also U.S. application Ser. No. 09/098,079). This embodiment may offer certain advantages by permitting both exmtDNA and mtDNA to be simultaneously quantified using a single oligonucleotide primer capable of hybridizing to a complementary nucleic acid target sequence present in a defined region of mtDNA and in a corresponding region of a exmtDNA sequence. (See U.S. application Ser. No. 09/098,079 for disclosure of nuclear exmtDNA pseudogenes having high homology to mtDNA gene sequences.) Without wishing to be bound by theory, the use of a single primer for quantifying exmtDNA and mtDNA is believed to avoid uncertainties associated with potential disparities in the relative hybridization properties of multiple primers and may offer other advantages. Where such a target sequence is situated adjacent to an exmtDNA nucleotide sequence position that is a nucleotide substitution, insertion or deletion relative to the corresponding mtDNA sequence position, primer extension assays may be designed such that oligonucleotide extension products of primers hybridizing to mtDNA are of different lengths than oligonucleotide extension products of primers hybridizing to exmtDNA. Accordingly, the amount of exmtDNA in a sample and the amount of mtDNA in the sample may be determined by quantification of distinct extension products that are separable on the basis of sequence length or molecular mass.

Sequence length or molecular mass of primer extension assay products may be determined using any known method for characterizing the size of nucleic acid sequences with which those skilled in the art are familiar. In a depicted embodiment, primer extension products are characterized by gel electrophoresis. In another embodiment, primer extension products are characterized by mass spectrometry (MS), which may further include matrix assisted laser desorption ionization/ time of flight (MALDI-TOF) analysis or other MS techniques known to those skilled in the art. See, for example, U.S. Pat. Nos. 5,622,824, 5,605,798 and 5,547, 835. In another embodiment, primer extension products are characterized by liquid or gas chromatography, which may further include high performance liquid chromatography (HPLC), gas chromatography-mass spectrometry (GC-MS) or other well known chromatographic methodologies.

For certain embodiments, input information is derived from generation and detection of oligonucleotide primer extension assay reaction products following resolution of multiplexed primer extensions on a 12% polyacrylamide electrophoretic gel, for example as described by Fahy et al. (*Nucl. Acids. Res.* 25:3102–3109, 1997). Briefly, fresh venous blood samples (3–4 mL) are drawn from subjects and the platelet/white blood cell fractions are isolated by centrifugal density sedimentation using HISTOPAQUE® 1077 density separation medium (Sigma, St. Louis, Mo.) in ACCUSPIN™ tubes (Sigma) according to the supplier's recommendations. After centrifugation at 1000×g for 10 min at room temperature, the plasma and white blood cell layers are transferred to clean tubes and sedimented at 7000×g for 10 min. White cell pellets are resuspended in 0.9% (w/v) NaCl, 1 mM ethylenediaminetetraacetic acid (EDTA, Sigma) and stored at −80° C. until use. To extract cellular DNA, the pellets are thawed and sedimented at 12,000×g for 5 min, washed once with 0.6 mL Dulbecco's phosphate buffered saline (PBS; Gibco-BRL, Grand Island, N.Y.), resuspended in 0.2 mL water and held in a boiling water bath for 10 min. Insoluble debris is sedimented by centrifugation at 14,000×g for 2 min, and DNA in the supernatant is quantified according to absorbance at 260 nm.

Amplification of cellular DNA target sequences for use as templates in primer extension assays is performed using polymerase chain reaction (PCR) as described (Fahy et al., 1997), where mtDNA encoding cytochrome c oxidase subunit 2 (COX2) and highly homologous exmtDNA sequences are amplified using described COX2 primers that are complementary to regions common to mtDNA and exmtDNA (see also, e.g., U.S. application Ser. No. 09/098, 079). Fluorescein 5'-labeled oligonucleotide primers are synthesized on an Applied Biosystems 394 DNA/RNA synthesizer (ABI Division, Perkin Elmer, Foster City, Calif.) using standard phosphoramidite chemistry and either 6-FAM or HEX Amidite reagent (ABI) in the last step of automated synthesis. Primers are purified by standard reverse-phase chromatography, and homogeneity is confirmed by electrophoresis on an ABI Model 373 Sequencer.

Mulitplexed primer extension assay reactions employ amplified COX2 mtDNA and highly homologous COX2-like exmtDNA templates prepared as just described, and the following 5'-fluoresceinated oligonucleotide primers:

| | | |
|---|---|---|
| P04b 5'- - TCC CCT ATC ATA GAA GAG CTT ATC A - - 3' | | SEQ ID NO:1 |
| P05  5'- - GGC CAA TTG ATT TGA TGG TAA - - 3' | | SEQ ID NO:2 |
| P06B 5'- - ATG TAA TTA TTA TAC GAA TGG GGG CTT CAA - 3' | | SEQ ID NO:3 |

Primers are diluted in 10 mM Tris-pH 8.5, 5 mM EDTA, and nucleotides are diluted in 10 mM Tris, pH 8.5, 2 mM $MgCl_2$. Nucleotides for use in the primer extension assay reaction are dATP, dCTP and the chain terminating dideoxynucleotides ddGTP and ddTTP (Amersham, Cleveland, Ohio). Primer extension assay reactions contain 1 µL of PCR amplified COX2 template DNA prepared as described above. In a total volume of 8 µL, the reaction contains template, 20 fmol fluorescein-labeled primer, 400 µM each of ddGTP and ddTTP, 25 µM each of dATP and dCTP and 0.6 U ULTMA™ thermostable DNA polymerase (Perkin Elmer, Norwalk, Conn.) in 10 mM Tris-HCl, pH 8.8, 10 mM KCl, 0.002% Tween 20, 2 mM $MgCl_2$. Control reactions include reaction mixtures containing primers in the absence of template, and a reaction using each template in a form known to be homogeneous (e.g., mtDNA without exmtDNA, and exmtDNA without mtDNA; optionally separate wildtype and mutant templates). After an initial denaturation step at 95° C. for 2 min, the reaction conditions comprise 20 cycles of 95° C. for 20 s and 55° C. for 40 s. Samples containing reaction products are concentrated to ~1 gL by heating open reaction tubes at 94° C. for 7 min, then 8 µL loading dye (0.5% blue dextran in 83% formamide, 8.3 mM EDTA, ph 8.0) are added to each sample and the samples are denatured for 3 min at 85° C.

Aliquots of 3 µL from each reaction are loaded onto an ABI Model 373 DNA Sequencer (ABI Division, Perkin-Elmer, Foster City, Calif.) equipped with a 12% denaturing polyacrylamide gel and Tris-borate-EDTA running buffer as specified by the instrument supplier. Electrophoresis and detection of fluorescent band intensities are conducted according to the instrument supplier's instructions, using the GENESCAN™ 672 software program (ABI) provided with the instrument. The multiplexed reactions produce extension products from mtDNA and exmtDNA templates that are unique in size and that are easily resolved by the electrophoretic apparatus (e.g., a biological assay device), which is capable of detecting products that differ in length by a single nucleotide to produce digitized signals corresponding to band peak and/or intensity values.

FIG. 1 and the following discussion provide a brief, general description of a suitable computing environment in which the invention can be implemented. Although not required, embodiments of the invention will be described in the general context of computer-executable instructions, such as program modules or macros being executed by a personal computer. Those skilled in the relevant art will appreciate that the invention can be practiced with other computer system configurations, including hand-held devices, multiprocessor systems, microprocessor-based or programmable consumer electronics, network PCs, mini computers, mainframe computers, and the like. The invention can be practiced in distributed computing environments where tasks or modules are performed by remote processing devices, which are linked through a communications network. In a distributed computing environment, program modules may be located in both local and remote memory storage devices.

Referring to FIG. 1, a conventional personal computer 100 includes a processing unit 102, a system memory 104 and a system bus 106 that couples various system components including the system memory to the processing unit. The processing unit 102 may be any logic processing unit, such as one or more central processing units (CPUs), digital signal processors (DSPs), application-specific integrated circuits (ASIC), etc. Unless described otherwise, the construction and operation of the various blocks shown in FIG. 1 are of conventional design. As a result, such blocks need not be described in further detail herein, as they will be understood by those skilled in the relevant art.

The system bus 106 can employ any known bus structures or architectures, including a memory bus with memory controller, a peripheral bus, and a local bus. The system memory 104 includes read-only memory ("ROM") 108 and random access memory ("RAM") 110. A basic input/output system ("BIOS") 112, which can form part of the ROM 108, contains basic routines that help transfer information between elements within the personal computer 100, such as during start-up.

The personal computer 100 also includes a hard disk drive 114 for reading from and writing to a hard disk (not shown), and an optical disk drive 116 and a magnetic disk drive 118 for reading from and writing to removable optical disks 120 and magnetic disks 122, respectively. The optical disk 120 can be a CD-ROM, while the magnetic disk 122 can be a magnetic floppy disk. The hard disk drive 114, optical disk drive 116 and magnetic disk drive 118 communicate with the processing unit 102 via the bus 106. The hard disk drive 114, optical disk drive 116 and magnetic disk drive 118 may include interfaces or controllers (not shown) coupled between such drives and the bus 106, as is known by those skilled in the art. The drives 114, 116 and 118, and their associated computer-readable media, provide nonvolatile storage of computer readable instructions, data structures, program modules and other data for the personal computer 100. Although the depicted personal computer 100 employs a hard disk, optical disk 120 and magnetic disk 122, those skilled in the relevant art will appreciate that other types of computer-readable media that can store data accessible by a computer may be employed, such as magnetic cassettes, flash memory cards, digital video disks ("DVD"), Bernoulli cartridges, RAMs, ROMs, smart cards, etc.

Program modules can be stored in the system memory 104, such as an operating system 124, one or more application programs 126, other programs or modules 128 and program data 130. The system memory 104 may also include a web browser 131 for permitting the personal computer 100 to access and exchange data with web sites in the World Wide Web of the Internet, as described below. The application programs 126 can include spreadsheet applications, such as Excel® by Microsoft Corp. While shown in FIG. 1 as being stored in the system memory 104, the operating system 124, application programs 126, other modules 128, program data 130 and web browser 138 can be stored on the hard disk of the hard disk drive 114, the optical disk 120 of the optical disk drive 116 and/or the magnetic disk 122 of the magnetic disk drive 118.

A user can enter commands and information into the personal computer 100 through input devices such as a keyboard 132 and a pointing device such as a mouse 134. Other input devices (not shown) can include a microphone, joystick, game pad, scanner, etc. These and other input devices are connected to the processing unit 102 through an interface 136 such as a serial port interface that couples to the bus 106, although other interfaces such as a parallel port, game port or universal serial bus ("USB") can be used. A monitor 138 or other display device is coupled to the bus 106 via a video interface 140, such as a video adapter. The personal computer 100 can include other output devices, such as speakers, printers, etc.

The personal computer 100 can operate in a networked environment using logical connections to one or more remote computers, such as a remote computer 150. The remote computer 150 can be another personal computer, a server, a router, a network PC, a peer device or other common network node, and typically includes many or all of the elements described above for the personal computer 100. Typically, the remote computer 150 includes a memory storage device such as a disk drive 152 shown in FIG. 1. The remote computer 150 is logically connected to the personal computer 100 under any known method of permitting computers to communicate, such as through a local area network ("LAN") 154 or a wide area network ("WAN") or Internet 156. Such networking environments are well known in offices, enterprise-wide computer networks, intranets and the Internet.

When used in a LAN networking environment, the personal computer 100 is connected to the LAN 154 through an adapter or network interface 158 (coupled to the bus 106). When used in a WAN networking environment, the personal computer 100 often includes a modem 160 or other device for establishing communications over the WAN/Internet 156. The modem 160 is shown in FIG. 1 as coupled between the interface 136 and the WAN/Internet 156. In a networked environment, program modules, application programs, or data, or portions thereof, can be stored in the remote computer 150, such as in the disk drive 152. Those skilled in the relevant art will readily recognize that the network connections shown in FIG. 1 are only some examples of establishing communication links between computers, and other links may be used, including wireless links.

A biological assay device 170, such as a DNA sequencer, can be coupled to the personal computer 100, such as through the interface 136. In one embodiment, a DNA sequencer such as, for example, an ABI model 373 (or later model), by Applied Biosystems Inc. ("ABI"), a division of Perkin Elmer, Foster City, Calif., with GENESCAN™ analysis software (version 2.2.1–2 or later, also by ABI) is employed with the personal computer 100. As noted above, one or more biological samples may be analyzed, such as primer extension products characterized by gel electrophoresis on a gel 172.

Figure 2:
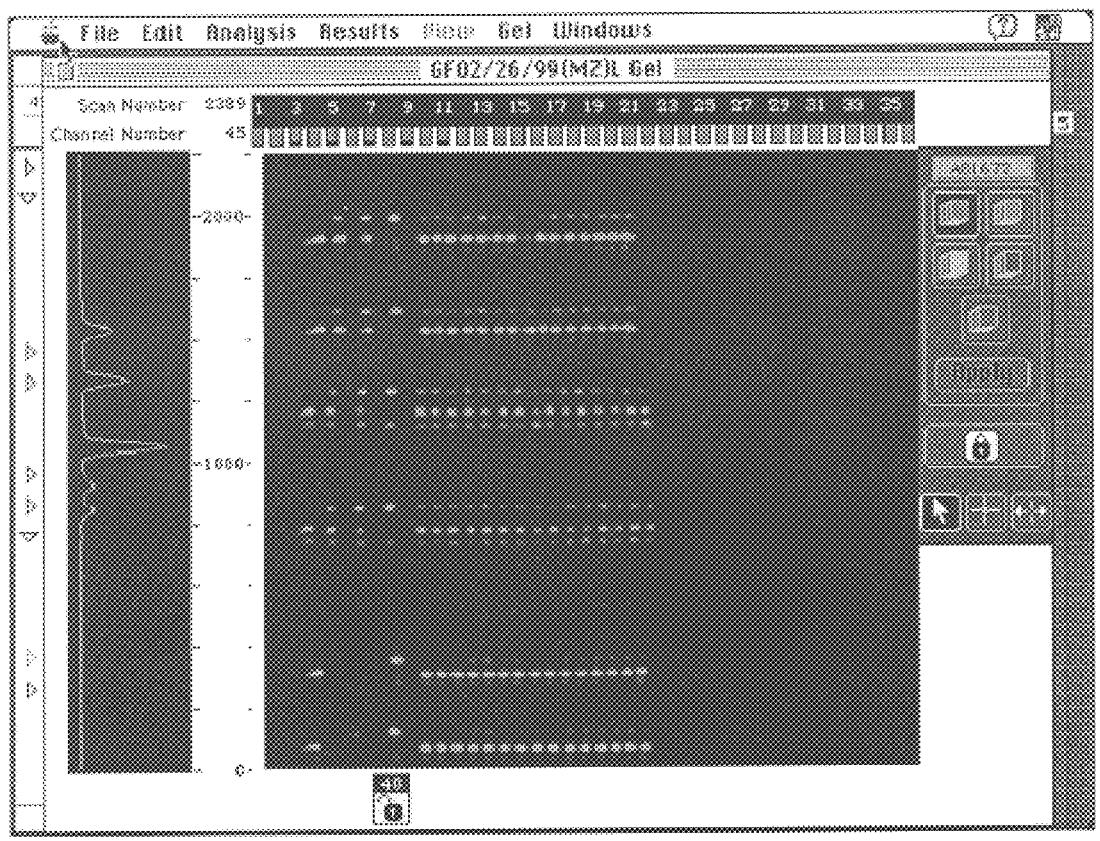
FIG. 2 is a digitized image of a gel plate depicting fluorescence-labeled oligonucleotides separated on the basis of size under gel electrophoresis.

Referring to FIG. 2, an example of a digitized image from a gel is shown, such as produced under the GENESCAN analysis software. The gel image of FIG. 2 depicts lanes 1 through 36 from left to right, and scan numbers from 0 to 2100 from bottom to top. Numerous samples are often time multiplexed with respect to a given gel. Numerous samples are shown in the gel image, each sample being distinguished by its lane number, and then scan lines within each lane. For example, the lowermost rows in FIG. 2 reflect the first set of samples injected into lanes 1–36.

Two control lanes, a mitochondrial control lane (lane 1), and a nuclear control lane (lane 7) provide base values or control points to identify corresponding rows of samples (lanes 9–36). At approximately scan number 80, a mitochondrial band is shown in the mitochondrial control lane (lane 1), and aligned therewith, in lanes 9–36, are corresponding mitochondrial test samples. Similarly, at approximately scan number 127, a nuclear band is shown in the nuclear control lane (lane 7), and in lanes 9–36, corresponding nuclear test sample bands. The gel 172 is imaged and analyzed by the DNA sequencer, whereby the sequencer produces output data based on image analysis of the gel image (e.g., the image of FIG. 2), as described below.

Those skilled in the relevant art will readily know how to load a gel and use the DNA sequencer, such as the DNA sequencer model noted above. As also described above, typically the products of multiplexed primer extension assay reactions may be analyzed, for example, on a 12% acrylamide gel capable of resolving products differing in length by a single nucleotide. However, depending on the particular sample set to be analyzed, other biological assay tools and biological assay device configurations may be routinely selected by those familiar with the art. Likewise, those skilled in the relevant art will readily know how to employ the corresponding GENESCAN™ analysis software to analyze the gel and produce peak or intensity values from the gel, such as the gel shown in FIG. 2. The GENESCAN analysis software, for example, produces an ASCII data file based on such analysis.

Figure 3A:
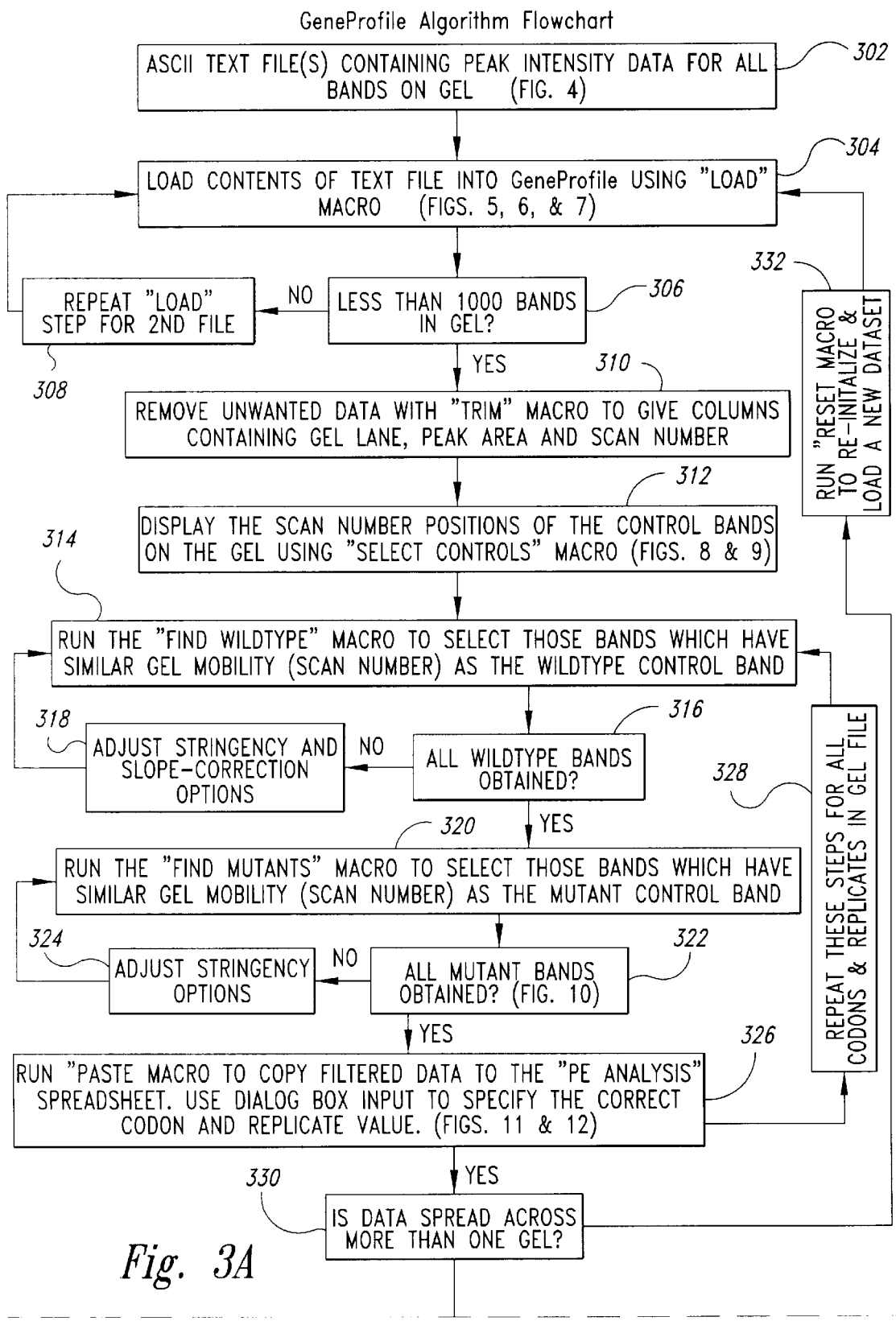
FIGS. 3A and 3B together form a flowchart depicting a method of analyzing image data produced from, for example, the gel plate of FIG. 2.
Figure 3B:
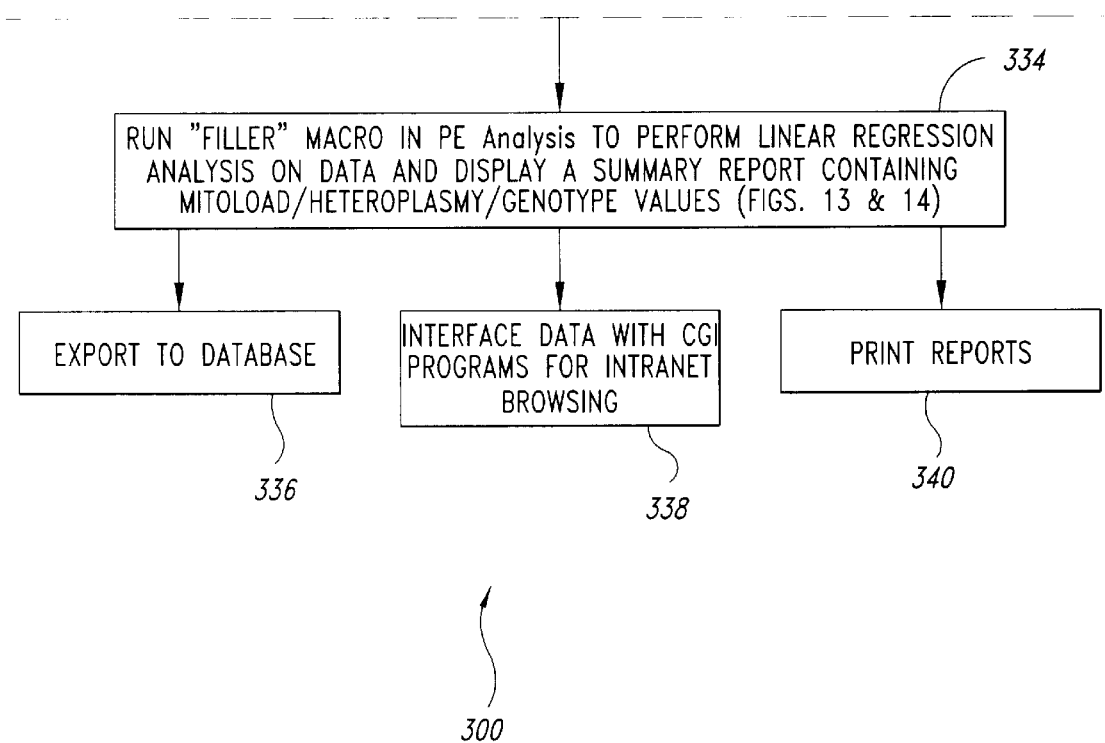

Referring to the flowchart of FIGS. 3A and 3B, a routine 300 performed by the personal computer 100 receives such an ASCII data file and analyzes the results of multiple primer extension products time multiplexed in rows of the gel. Unless described otherwise herein, the steps depicted in FIGS. 3A and 3B are well known or described in detail in source code macros described in the above-noted and cross-referenced provisional patent application. Indeed, much of the detailed description provided herein is disclosed in the provisional patent application; most additional material will be recognized by those skilled in the relevant art as being inherent in the detailed description provided in such provisional patent application or well known to those skilled in the relevant art based on the detailed description provided in the provisional patent application. Those skilled in the relevant art can create source code (such as in Visual Basic), microcode or program logic arrays or firmware based on the flowchart of FIG. 3 and the detailed description provided herein. The routine 300 can be stored in the system memory 104 and/or non-volatile memory such as the magnetic disk 122.

The routine 300 can be written as one or more modules or macros written in Visual Basic for the spreadsheet application. In one embodiment, the routine includes two spreadsheet templates, GeneProfile2 and PE Analysis Template2, which include seven and one Visual Basic macros, respectively. The GeneProfile2 template allows a user to import the ASCII data file and perform filtering operations to extract and process signal or peak intensity data. The GeneProfile2 template uses mobility values to identify and filter two or more sets of analytes that have the same gel lane values, and thereby process the raw ASCII text data and extract wild-type/mitochondrial and mutant/nuclear band intensities for codons of interest in the gel 172.

Figure 4:
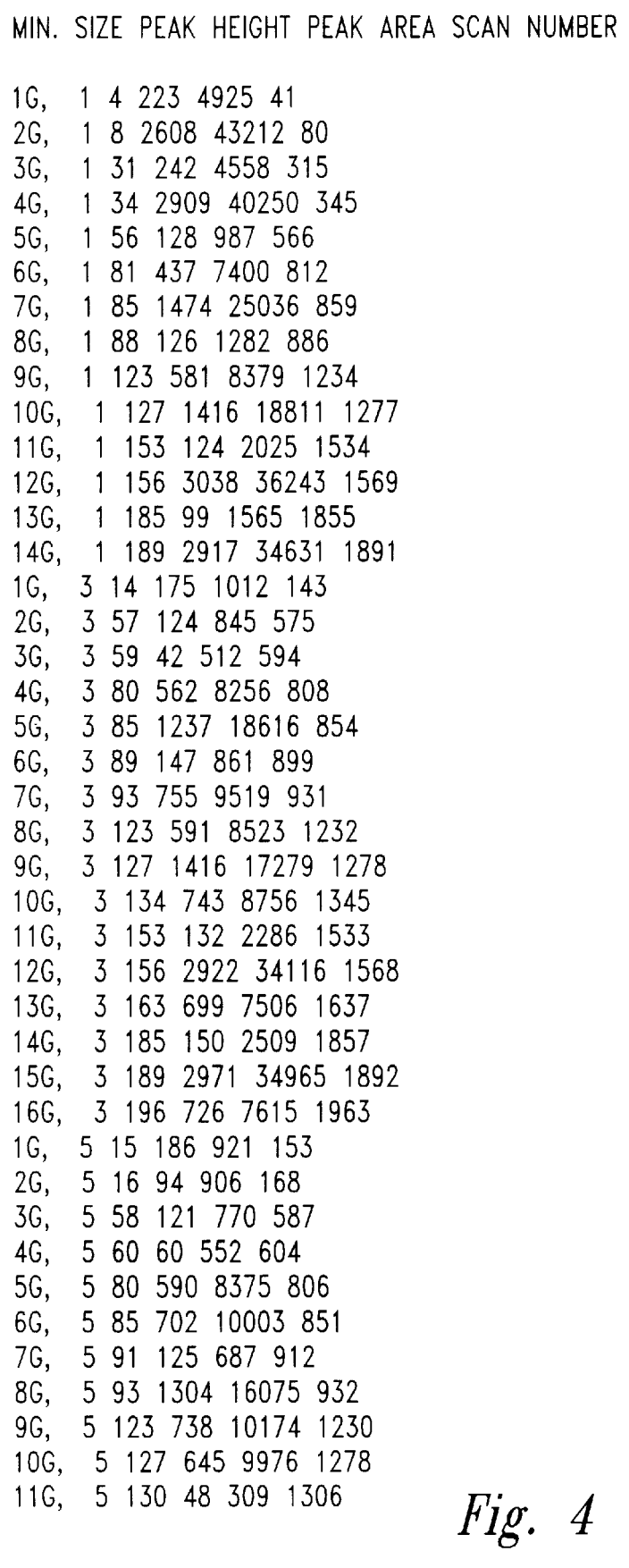

In step 302, the ASCII data file containing peak intensity data for all bands on the gel 172 are input to the routine 300 running on the personal computer 100. An example of an ASCII data file output from the GENESCAN analysis software is shown in FIG. 4. Such an ASCII data file can be stored on removable media, such as the magnetic disk 122, or be input from the LAN 154 if the personal computer 100 is coupled to another computer that itself is coupled to the DNA sequencer or biological assay device 170. Alternatively, the ASCII data file can be input serially to the personal computer 100 via the interface 136 directly from the biological assay device 170. As shown in FIG. 4, the ASCII data file contains a set of numbers which essentially describe three parameters: an X coordinate, a Y coordinate, and a Z coordinate. The X coordinate refers to the gel lane on which the sample containing that peak was run (e.g., lane 1 through 36). The Y coordinate is a number describing the electrophoretic mobility of the peak (e.g., time in minutes or seconds, or by scan number 0–2100). The Z coordinate represents a peak height or peak intensity value. A high peak intensity value represents a bright band or high abundance of analyte, while a low intensity value may represent a spurious peak or noise in the gel ASCII data file.

The PE Analysis template receives the data processed by the GeneProfile2 template, performs calculations to determine relative abundance of analytes under investigation, normalizes the data using linear regression and curve-fitting algorithms, and summarizes the results for each test sample. More specifically, the PE Analysis template calculates or normalizes peak height or area ratios from these two or more sets and uses curve fitting. The PE analysis Template2 template summarizes data for each sample in terms of relative abundance of the two or more detectable analytes, which may be a wild-type/mutant (or mitochondrial/nuclear) designation, percent heteroplasmy value, genotype designation or the type. The terms "wild type" and "mitochondrial," and "mutant" and "nuclear" are used generally interchangeably herein.

Figure 5:
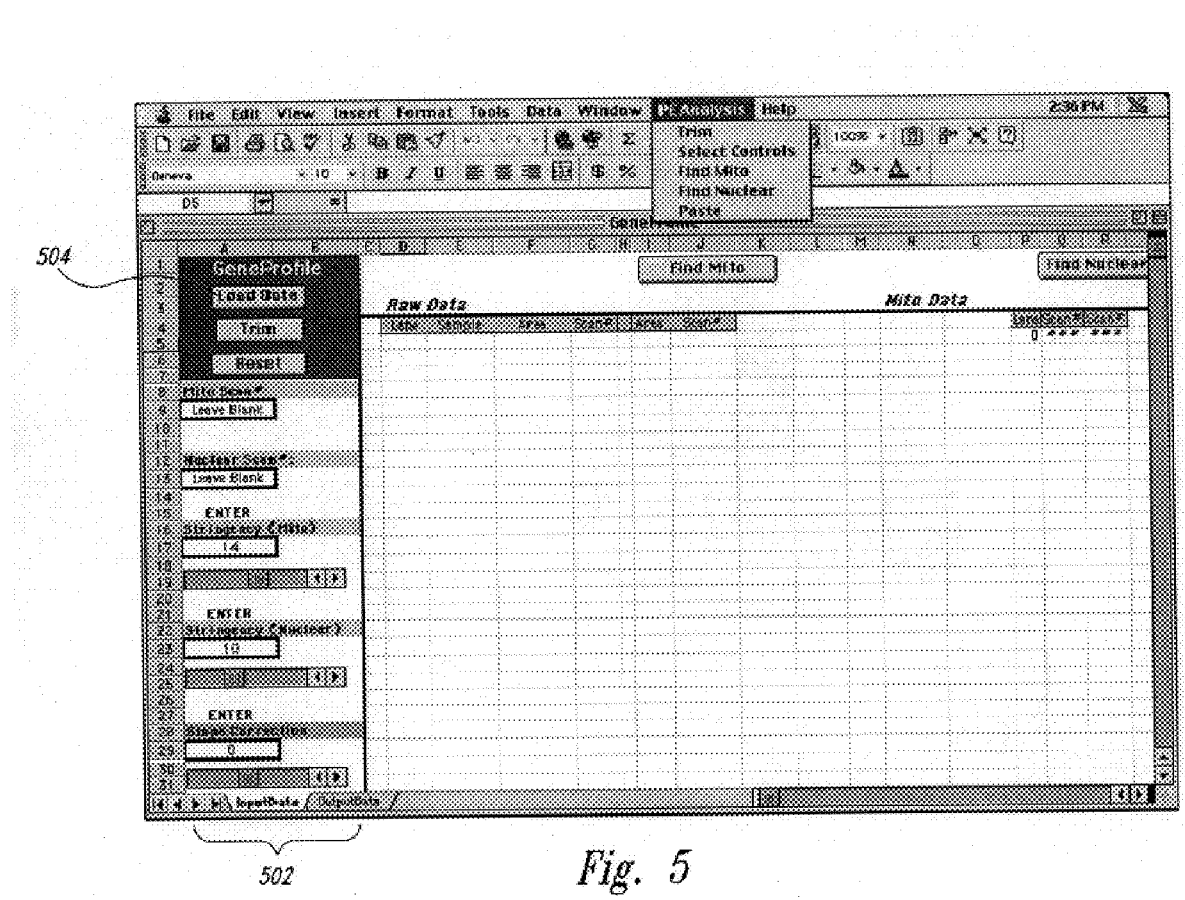
FIG. 5 is an initial display screen before raw input data has been input thereto.

In step 304, the user opens the GeneProfile2 template under the spreadsheet application, which can produce a screen display such as that shown in FIG. 5. As shown in FIG. 5, a drop-down menu "PE Analysis" includes the following commands: Trim, Select Controls, Find Mito, Find Nuclear and Paste, all of which are described below. Additionally, the GeneProfile2 template includes a left-hand control section 502 that includes the following buttons: load data, trim and reset, also described below. Furthermore, the control section 502 includes data input sections for mitochondrial and nuclear control scan numbers, and slider bar controls for stringency (mito), stringency (nuclear) and slope correction, also described below.

Figure 6:
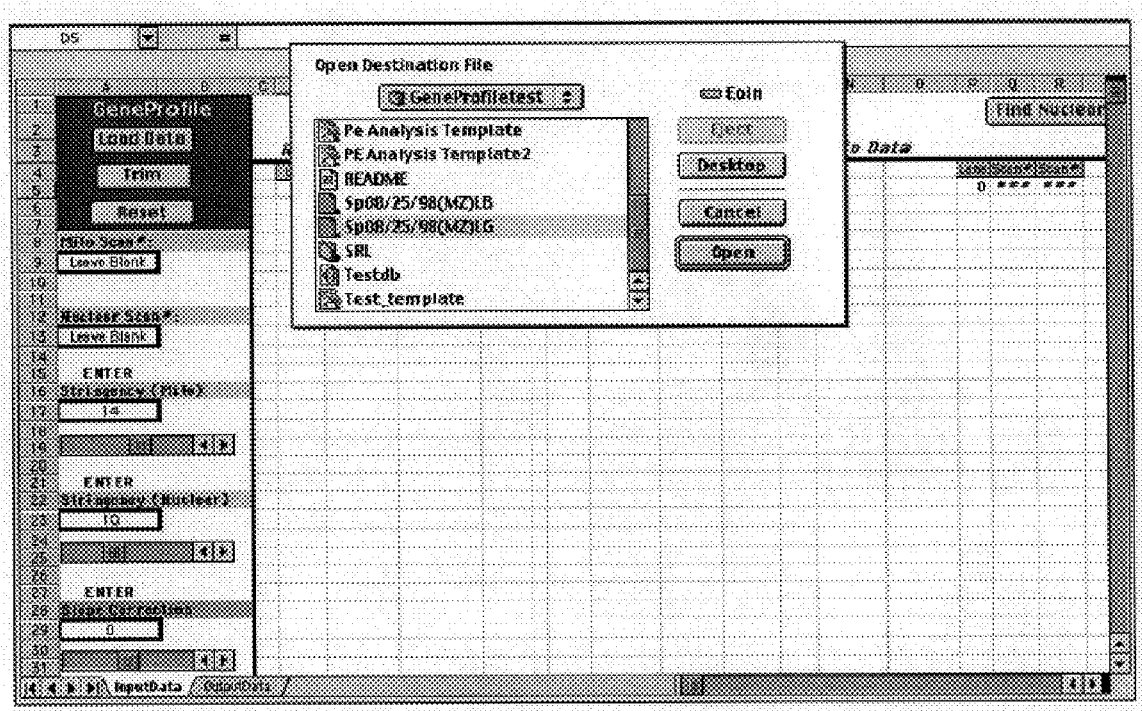
FIG. 6 is a display screen showing a dialogue box for selecting and loading raw input data, such as the data of FIG. 4.
Figure 7:
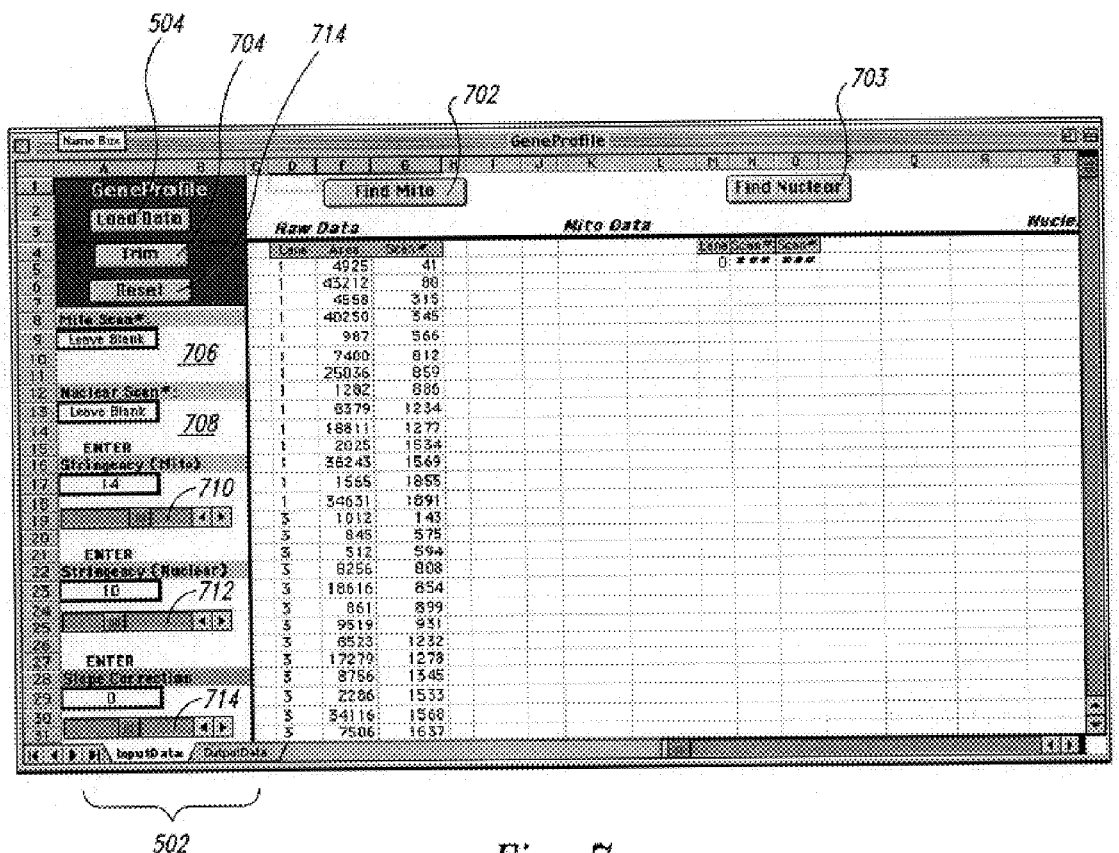
FIG. 7 is a display screen showing the raw input data of FIG. 4.

Selecting load data button 504 in the control section 502 of the screen shown in FIG. 5 loads the ASCII data file into the spreadsheet work area (shown as columns D–J and rows 5 onward). Selecting the load data button results in a dialog box to be opened that permits the user to select a desired ASCII text file, as shown in FIG. 6. The user can select the load data button using many known computer input techniques, such as moving the mouse 134 to move the cursor over the load data button and depressing a button on the mouse, as is known by those skilled in the art. The load data button initiates a LoadMacro macro that reads the ASCII data file and properly inserts the data file into the appropriate rows and columns of the spreadsheet. For example, the ASCII data file may include tab delimited data, with each row of tab delimited data defined by a carriage return. The LoadMacro macro then simply identifies each data sample in a row, separated by tabs, and places it in a corresponding column for a given row in the spreadsheet, as is known by those skilled in the art. FIG. 7 shows the ASCII data file of FIG. 4 imported and loaded into the spreadsheet.

In step 306, it is determined whether the gel has less than 1000 bands. For example, the user could determine the number of bands, or alternately the routine 300 could automatically make the determination. If the gel has 1000 or more bands, then the above load data operations are again performed under steps 308 and 304.

In step 310, the user selects Trim button 704 in the controls portion 502 of the screen, such as shown in FIG. 7. The trim button 704 initiates a TrimMacro macro, which removes unwanted fields from the imported raw ASCII text data. For example, peak intensity can be present in the ASCII data file as both peak height and peak area. However, only one variable is required for analysis. Therefore, the TrimMacro macro simply determines whether more than three columns of data are provided, and if so, such columns are simply deleted. As a result, the raw input data includes only three columns: lane number, peak area and scan number. Additionally, the Trim Macro macro deletes redundant data such as when the gel 172 contains more than 1,000 bands, and the input data is spread across two ASCII data files. The Trim Macro macro, in this case, identifies the last row of data in the first ASCII data file and looks for the corresponding row in the second input ASCII data file. This redundant row, and all duplicate rows are then deleted in the second ASCII data file. In an alternate embodiment, the routine 300 could automatically determine whether the TrimMacro macro should be executed, and could automatically execute the macro when appropriate.

FIG. 7 shows a "Find Mito" button 702, a "Find Nuclear" button 703 and mito and nuclear control scan number input boxes 706 and 708, respectively, all described below. Also shown in FIG. 7 are slider bars 710, 712 and 714 which correspond to controls for adjusting mitochondrial and nuclear stringency values in the slow correction value, also discussed below. A InitializeDB macro generates and displays the user input dialog box.

Figure 8:
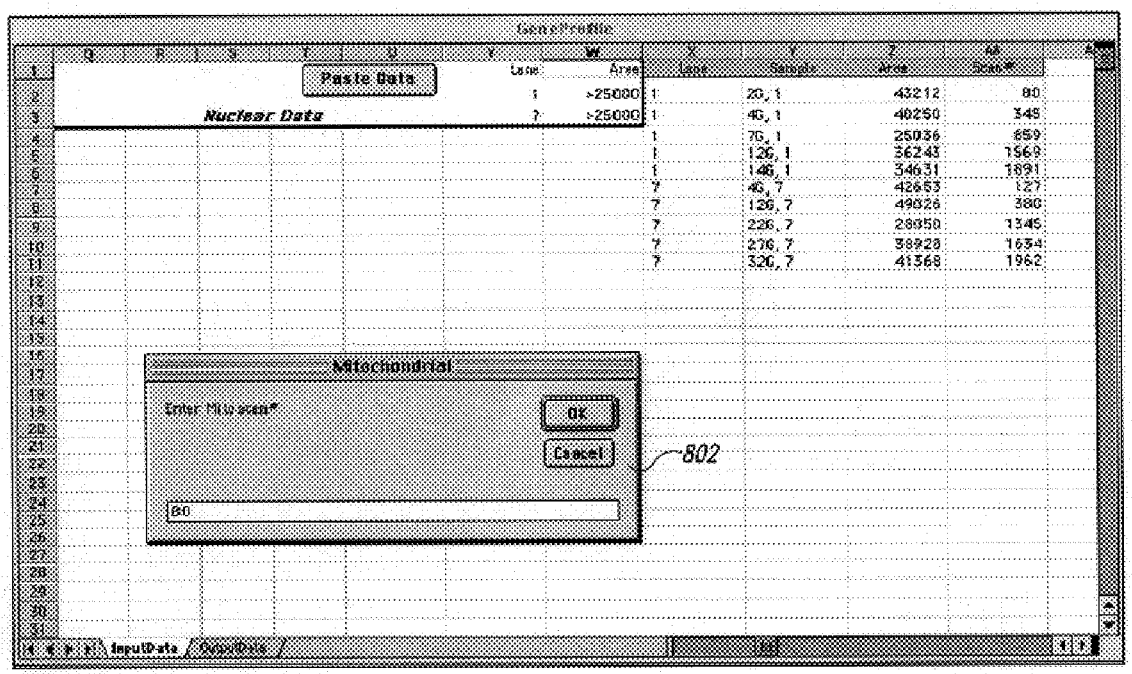
FIG. 8 is a display screen showing a dialogue box for entering a mitochondrial control scan number.
Figure 9:
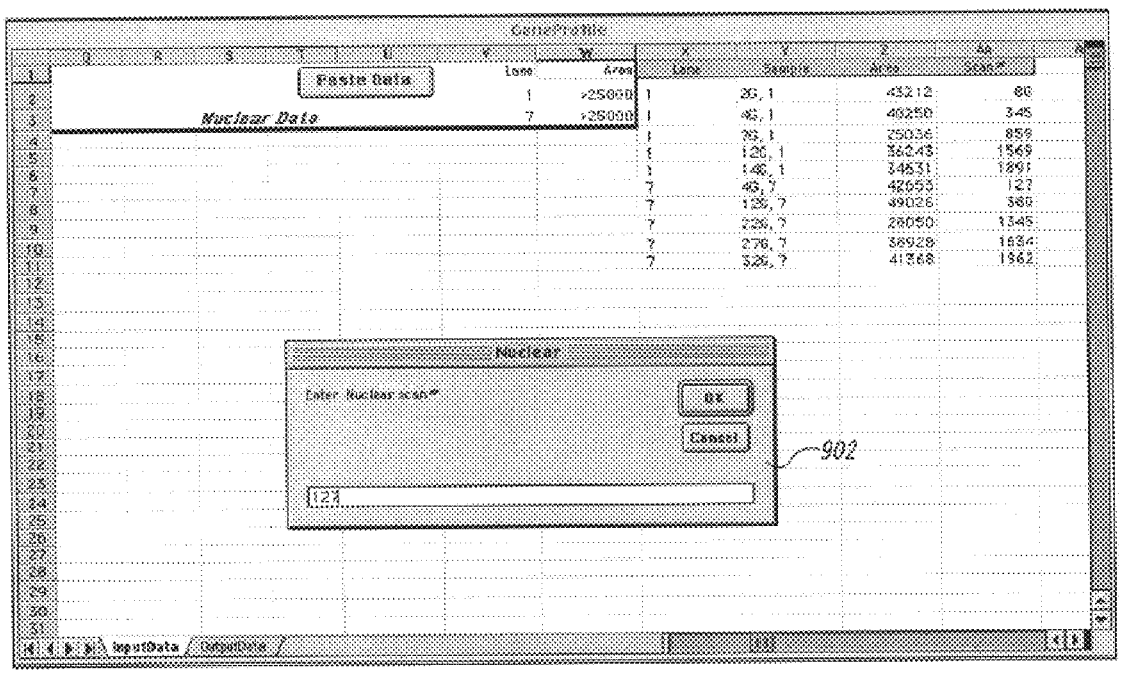
FIG. 9 is a display screen showing a dialogue box for entering a nuclear control scan number.

In step 312, the user inputs the scan numbers for the mitochondrial and nuclear controls in the gel (lanes 1 and 7 of FIG. 2). A GetControls macro retrieves mobility or scan number values for the control samples with a peak area greater than a specified threshold value, and then displays the retrieved values. The peak area threshold value is typically set at 20000, but may be lower or higher than this value depending on the nature and concentration of the fluorescent label used in the gel electrophoresis step. The lane numbers, sample designations, peak areas and scan numbers for control bands in the gel are loaded into a portion of the spreadsheet, such as in columns X-AA, respectively (shown in FIG. 8), under the GetControls macro. By selecting the Select Controls command in the PE Analysis menu (FIG. 5), a mitochondrial scan number dialog box 802 appears as shown in FIG. 8. The user can then identify the scan number for the first sample in column AA (having a value of 80) and input this value into the dialog box. Alternatively, the user can input the mitochondrial control scan number in the input box 706 (shown in FIG. 7). The same procedure is performed to enter the nuclear control scan number. Referring to FIG. 9, the scan number for the first row (sample) has a scan number of 127, which is input to a corresponding dialog box 902. The routine 300 in step 312 can display the dialog boxes 802 and 902 for the user to manually input scan numbers for the mitochondrial and nuclear controls. Alternatively, the routine 300 in step 312 can automatically identify such scan numbers by identifying peaks or areas greater than a threshold value of, for example, 20000, and then extracting the corresponding scan numbers for such peaks. As a result, spurious peaks or noise in the control lanes are filtered.

In step 314, the routine 300 runs a macro or module to filter or find wild type/mitochondrial bands having similar gel mobility (i.e., similar scan numbers) as the mitochondrial control scan number. The users finds or filters such mitochondrial bands by either selecting the "Find Mito" button 702 (FIG. 7) or selecting the "Find Mito" command in the PE analysis drop down menu (FIG. 5). A GSFilter macro thereby executes, which identifies all rows of data having a scan number similar to the mitochondrial control scan number previously entered in step 312, and identifies corresponding peak or area data for that row. A stringency value determines how similar the scan number must be to the previously entered mitochondrial control scan number. A default stringency value is set at 14, as shown in FIG. 7, but the slider bar 710 allows the user to adjust the stringency value. Thus, with a default stringency value 14, the GSFilter macro identifies all rows in column G having a scan number of 80 plus or minus 14 (i.e., 66–94).

In practice, most polyacrylamide gels exhibit a slight "frown," i.e., the bands at the center of the gel runs slower (and therefore have higher scan number values) than those near the edges. To compensate for this effect, the GSFilter macro provides a slope correction tool. The default slope correction value is zero, but the slider bar 714 allows the user to adjust this value for such a condition in the gel (e.g., setting the slope correction to 0.25). Under such a slope correction, the GSFilter macro automatically increases or decreases the control scan numbers when analyzing between different lanes across the gel.

Figure 10:
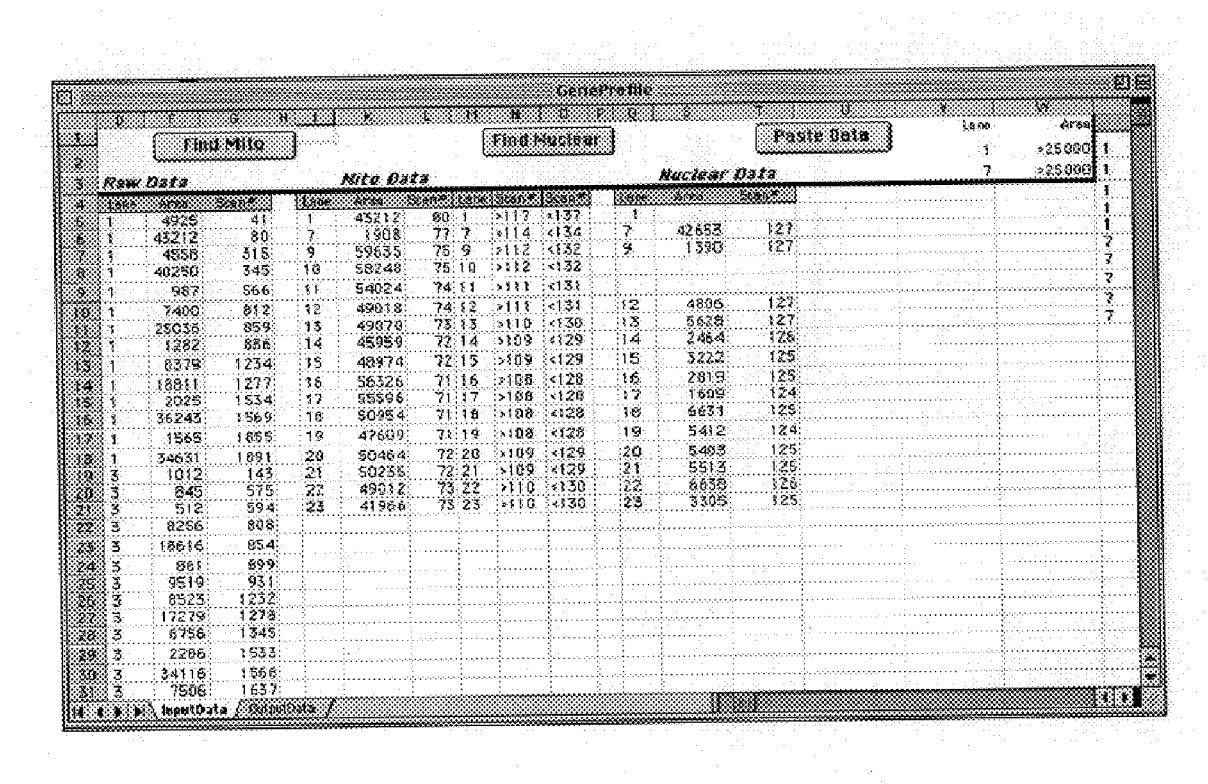

After filtering or extracting the appropriate data, the WtRow macro then parses, copies and pastes such rows to another predetermined location in the spreadsheet (such as cell I5 through cell L21 in FIG. 10, for this example). In step 316, the routine 300 determines whether all mitochondrial bands have been obtained. This may be done automatically, or empirically through observation of the user or previous knowledge of a number of bands that should be found.

If not all bands had been obtained, then in step 318 stringency and slope correction option values are modified. For example, the user can move the slider bars 710 and 714 to adjust the mito stringency and slope correction values, or the routine 300 can automatically adjust such correction under an interactive process to obtain the correct number of mitochondrial bands.

In step 320, the GSFilter macro similarly identifies all nuclear bands by identifying all rows having scan numbers similar to the previously entered nuclear control scan number. A Mutant Row macro then parses, copies and pastes to another part such identified rows of the spreadsheet (e.g., cell Q5 through cell T21 in FIG. 10, in this example.) In step 322, the user, or the routine 300, determines whether all nuclear bands have been obtained, such as by analyzing the spreadsheet of FIG. 11, which shows all identified bands (rows of data) pasted at a designated location in the spreadsheet. If not all nuclear bands have been obtained, then in step 324 the user or the routine 300 can adjust the slope correction or stringency values, such as by adjusting the slider bar 714, or slider bar 712, respectively. In steps 318 or 324, the user may also manually delete rows of spurious data using known techniques, such as using the command-K keystroke to manually filter out too many or too few peaks. As this point in the routine 300, all bands of interest, and their corresponding peaks or intensity values, should be identified and filtered from all other noise or spurious peaks in the ASCII data file.

Figure 11:
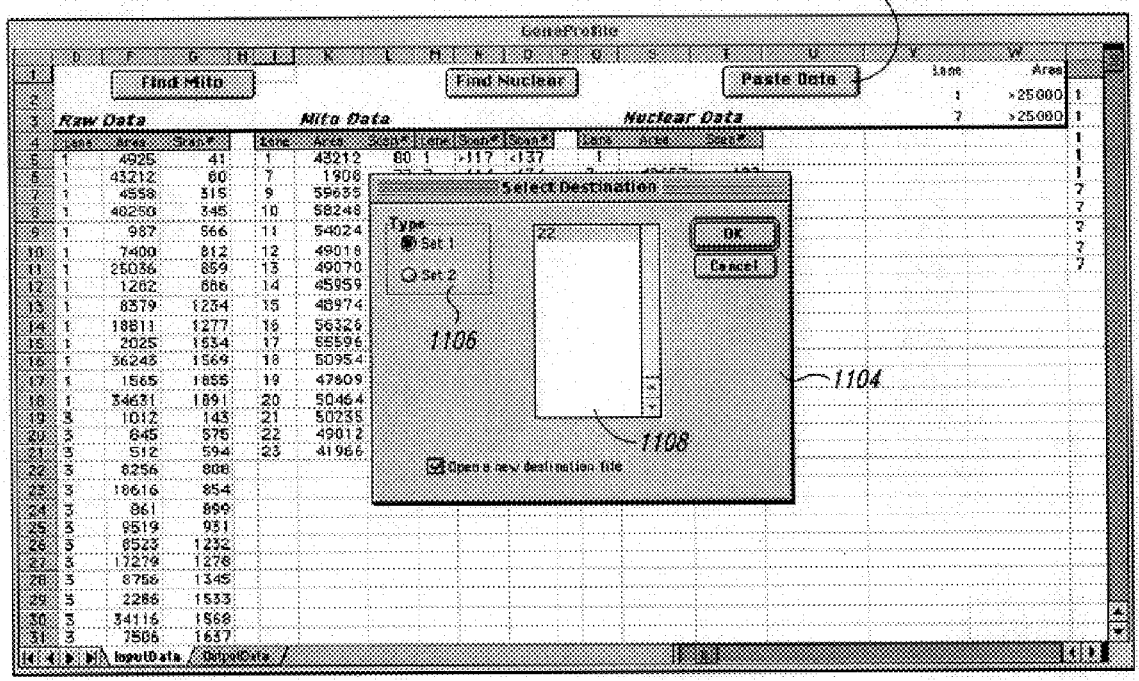
FIG. 11 is a display screen showing a dialogue box for designating output data.
Figure 12:
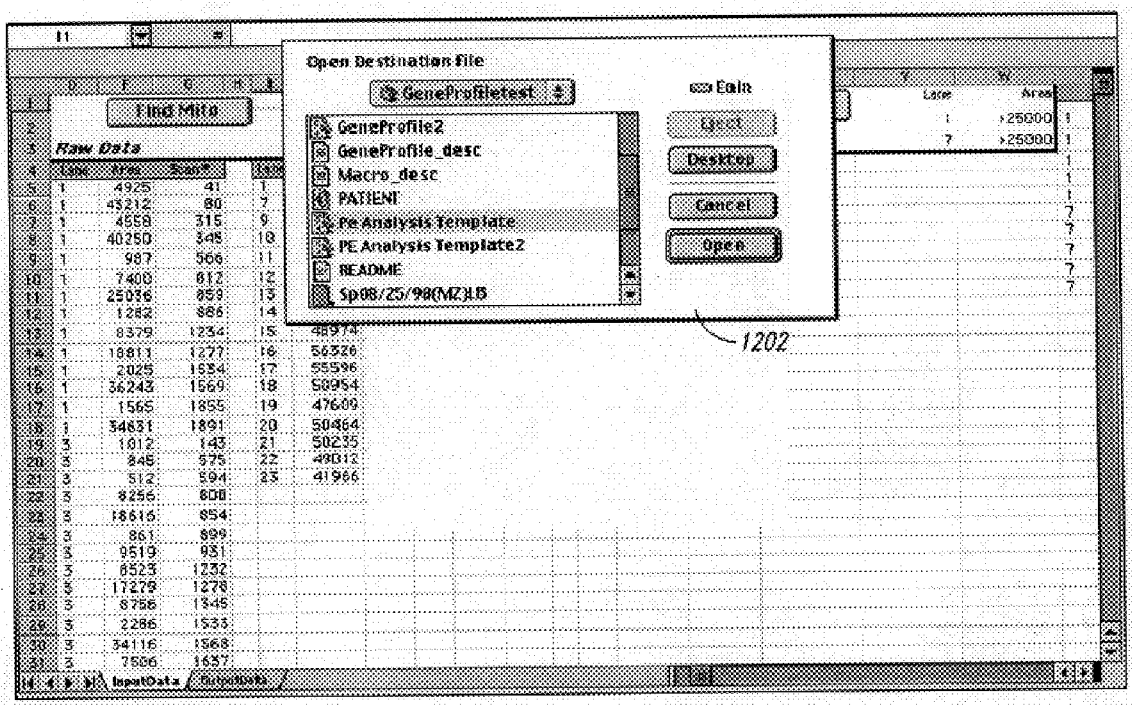
FIG. 12 is a display screen showing a dialogue box for selecting a destination file for the output data.

In step 326, the routine 300 performs a Paster macro to copy such filtered data to the PE analysis spreadsheet. The user can execute the Paster macro by selecting "Paste Data" button 1102 in FIG. 11, or selecting the "Paste" command in the PE Analysis drop-down menu (FIG. 5). The Paster macro selects the filtered data sets in the predetermined locations of the spreadsheet, and copies them to a predetermined location in the PE Analysis template. As shown in FIG. 11, a dialog box 1104 is displayed under step 326, which provides one or more codons and type sets to be selected. Since most biological assays are performed with duplicate samples, the user may chose between set 1 or set 2 in a button box 1106. Additionally, the user can select between one or more codons, such as codon 22, in a selection box 1108. If the PE Analysis template is not already open, then the user can open this destination file, such as shown by a dialogue box 1202 in FIG. 12.

If not all codons and reaction sets or duplicates have been selected under step 328, then steps 314 through 326 are repeated.

In step 330, the routine 300 determines whether any input data is spread across more than one gel. For example, the user may have two or more gels with samples to be analyzed. If so, then in step 332, the routine 300 performs a Reset macro to reinitialize and load a new data set. To perform such a reset, the user can depress a reset button 714 (FIG. 7). Under the Reset macro, the data in the GeneProfile template is deleted, and steps 304 through 330 are again performed. After all the data has been transferred (under steps 326 or 330) the GeneProfile template can be closed without need for performing a save function; the desired filtered data should all now be pasted within the PE Analysis template. The data sets for each loading can be manipulated in the GeneProfile template by clicking on the output data tab at the bottom of the screen and pressing a retrieve button (not shown) to view the data being exported to the PE Analysis template.

Figure 13:
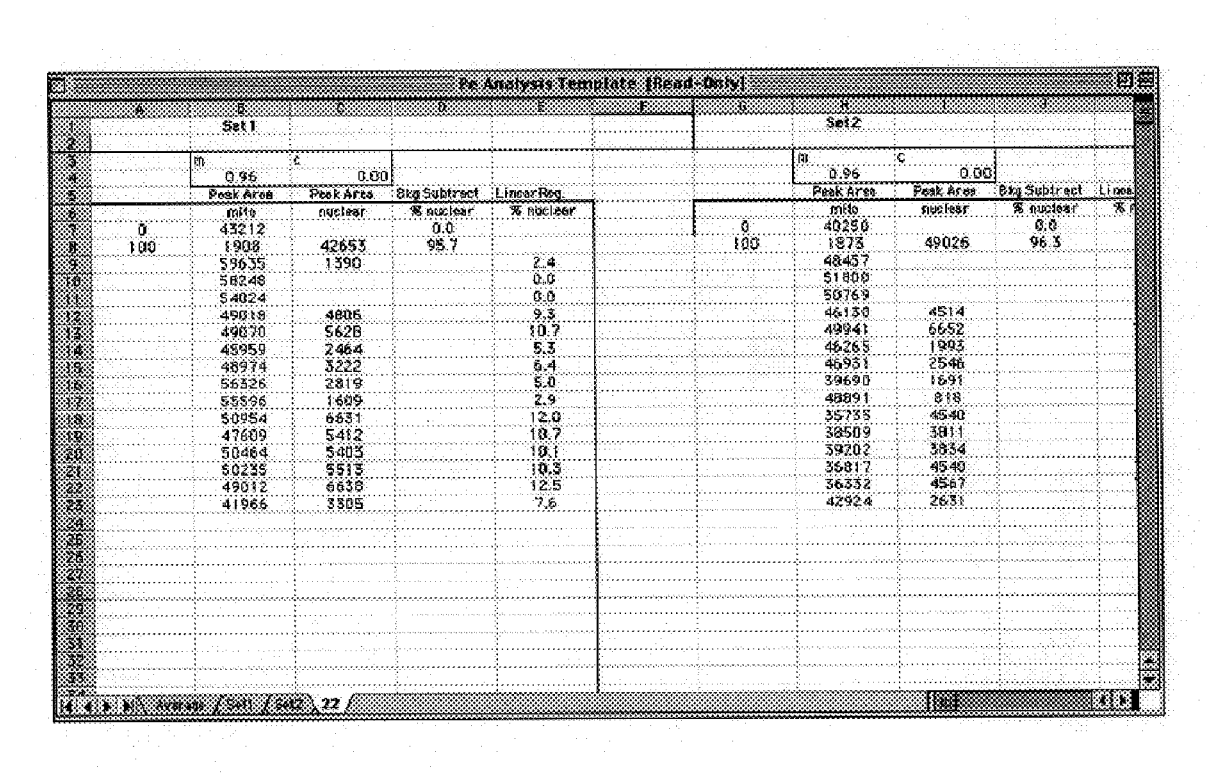

In step 334 shown in FIG. 3B, the routine 300 performs a Filler macro under the PE Analysis template to perform linear regression analysis on the filtered data and display a summary report containing desired values. Referring to FIG. 13, the filtered data for mitochondrial (e.g., primer extension product complementary to mtDNA or wildtype template) and nuclear (e.g., primer extension product complementary to exmtDNA or mutant template) peak areas, for sets 1 and 2, are shown pasted into the spreadsheet. The spreadsheet also shows a percent nuclear load for the samples. Selecting the "average" tab in the screen of FIG. 13 causes the routine 300 to display the screen of FIG. 14, which lists a summary sheet of mitochondrial load (e.g., value r as described above), as an average of the duplicates, for the samples. Corresponding patient ID and gel lane values are also provided. The screen of FIG. 14 also provides Sequencer and Loaded By input boxes 1402 and 1404, respectively, that permit the user to identify the particular sequencer and technician who loaded the sample.

The Filler macro effectively performs a straight line plot between 0 and 100 for the filtered values using well known linear regression and curve fitting algorithms. In general, once the relevant data has been filtered from the ASCII data file, any of a variety of analysis algorithms can be performed on the filtered data.

Following step 334, the analyzed data may be exported or used in a variety of applications. For example, in step 336, the processed data may be exported to a data base and stored for future use or analysis with larger data sets. In step 338, the analyzed data may be imported to common gateway interface ("CGI") programs or scripts to permit the data to be exchanged or manipulated via the Internet 156. In step 340, the analyzed data may be output to a printer for generating reports.

The above description of embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other systems, not necessarily the DNA sequencer and gel electrophoresis system described above.

The various embodiments described above can be combined to provide further embodiments. All of the above U.S. patents and applications are incorporated herein by reference in their entireties. Aspects of the invention can be modified, if necessary, to employ the systems and concepts of the various patents and applications described above to provide yet further embodiments of the invention.

These and other changes can be made to the invention in light of the above detailed description. While certain embodiments are described above as identifying and filtering intensity values from a data file produced from a gel, the invention can extract desired values in a data file produced from any known biological assay or testing device. While the bands on the gel, and their corresponding intensity values, are spatially differentiated from each other on the gel, the intensity values, or other desired values, could be distinguished based on time or frequency. These and other changes can be made to the invention in light of the above detailed description. In general, in the following claims, the terms used should not be construed to limit the invention to the specific embodiments disclosed in the specification and the claims, but should be construed to include all biological data analysis systems that operate under the claims to provide a method for efficiently analyzing data from such systems. Accordingly, the invention is not limited by the disclosure, but instead the scope of the invention is to be determined entirely by the following claims.

What is claimed is:

1. A system for generating information based on biological samples, comprising:

a biological assay device that analyzes a two dimensionally spaced set of biological samples and produces a set of data therefrom, wherein the biological samples include at least one control sample, wherein the set of data includes x-axis and y-axis spatial coordinate values and a quantitative value for each biological sample, and wherein the set of data may include unwanted values; and a computer having a processor and memory, wherein the computer receives the set of data from the biological assay device, stores the set of data in the memory, and wherein the processor:
  determines a two dimensional location of the at least one control sample based on the set of data;
  identifies x-axis and y-axis spatial coordinates for the biological samples in the set of data based on the determined two dimensional location of the at least one control sample;
  filters the quantitative values of for at least some of the biological samples, from the unwanted values, in the set of data, based on the identified x-axis and y-axis spatial coordinates; and
analyzes the filtered quantitative values of each biological sample, respectively, by comparing the quantitative value of a first portion of the filtered quantitative values of each respective biological sample at a first pair of x-axis and y-axis spatial coordinates with a sum of the quantitative value of the first portion and the quantitative value of a second portion of the filtered quantitative values of each respective biological sample at a second pair of x-axis and y-axis spatial coordinates to produce a displayable report of the analyzed quantitative values.

2. The system of claim 1 wherein the biological assay device includes a DNA sequencer for analyzing an electrophoresis gel having lanes and rows of mitochondrial and extramitochondrial samples, and an as say computer coupled to the DNA sequencer that produces the set of data identifying lanes, scan numbers and intensity values for each sample, wherein at least one predetermined lane includes a plurality of mitochondrial and extramitochondrial control samples, and wherein the processor receives input regarding scan numbers of the mitochondrial and extramitochondrial control samples.

3. The system of claim 1 wherein the biological assay device includes a DNA sequencer for analyzing an electrophoresis gel having lanes and rows of mitochondrial and extramitochondrial samples, and an assay computer coupled to the DNA sequencer that produces the set of data identifying lanes, scan numbers and quantitative values for each sample, and wherein the processor provides a slope correction when filtering the quantitative values.

4. The system of claim 1 wherein the x-axis and y-axis spatial coordinates in the set of data correspond to lanes and scan numbers of an electrophoresis gel, and wherein the processor:
  identifies the x-axis and y-axis spatial coordinates for the biological samples in the set of data based on determined lane and scan numbers of the at least one control sample and,
  identifies scan numbers for the biological samples that are within a predetermined stringency amount of the scan number of the at least one control sample.

5. The system of claim 1 wherein the biological assay device includes a DNA sequencer for analyzing an electrophoresis gel having lanes and rows of mitochondrial and extramitochondrial samples, and wherein the processor determines a percent mitochondrial load of the biological samples based on the filtered quantitative values.

6. The system of claim 1 wherein the computer includes a network interface, and wherein the computer is coupled to the biological assay device through the network interface.

7. The system of claim wherein the computer includes a web browser, and wherein the displayable report is provided to the web browser for transmission over the Internet.

8. The system of claim 1 wherein the computer includes a spreadsheet application, and wherein the processor executes at least one macro for the spreadsheet application that performs the identifying x-axis and y-axis values and the filtering of the quantitative values.

9. The system of claim 1 wherein the processor provides slope correction and stringency adjustments for filtering the quantitative values.

10. A method for generating information based on biological samples, comprising:
  receiving a set of data produced from testing a set of biological samples, wherein the biological samples include test samples and at least one control sample related to at least some of the test samples by space, time or frequency, wherein the set of data includes first and second values and a quantitative value for each test sample;
  identifying first or second values corresponding to the control sample in the set of data;
  identifying first or second values for at least some of the test samples in the set of data based on the identified first or second values of the control sample and the spatial, temporal or frequency relationship between the control sample and the at least some of the test samples;
  filtering the quantitative values for the at least some of the test samples in the set of data based on the identified first or second values; and
  analyzing the filtered quantitative values of a selected test sample by comparing the quantitative value of a first portion of the filtered quantitative values of the selected test sample at a first pair of x-axis and y-axis spatial coordinates with a sum of the quantitative value of the first portion and the quantitative value of a second portion of the filtered quantitative values of the selected test sample at a second pair of x-axis and y-axis spatial coordinates.

11. The method of claim 10 wherein the first and second values in the set of data identify lanes and row numbers, respectively, for spatially distinguishing mitochondrial and extramitochondrial test samples, wherein the quantitative values include intensity values for test samples, wherein at least one predetermined lane includes a plurality of mitochondrial and extramitochondrial control samples, and wherein identifying first or second values corresponding to the control sample includes receiving input regarding row numbers of the mitochondrial and extramitochondrial control samples for the set of data, and wherein identifying first or second values for at least some of the test samples includes identifying row numbers based on a preselected lane number for the mitochondrial and extramitochondrial test samples.

12. The method of claim 10 wherein receiving includes receiving the set of data from a DNA sequencer that analyzes an electrophoresis gel having lanes and rows of mitochondrial and extramitochondrial samples, and wherein the first, second and quantitative values in the set of data correspond respectively to lanes, scan numbers and intensity values for each test sample.

13. The method of claim 10 wherein the first and second values correspond respectively to lanes and scan numbers of an electrophoresis gel.

14. The method of claim 10 wherein the first and second values correspond respectively to x-axis and y-axis spatial coordinates.

15. The method of claim 10 wherein analyzing the filtered quantitative values includes determining a percent mitochondrial load of the biological samples based on the filtered quantitative values.

16. The method of claim 10 wherein the first and second values correspond respectively to lanes and scan numbers of an electrophoresis gel, and wherein the method includes providing a slope correction when filtering the quantitative values.

17. The method of claim 10 wherein the first and second values in the set of data correspond to lanes and scan numbers of an electrophoresis gel, and wherein the method includes:
    identifying a lane for the test samples in the set of data based on determined lane and scan numbers of the control sample; and, identifying scan numbers for the test samples that are within a predetermined stringency amount of the scan number of the control sample.

18. The method of claim 10 wherein the first and second values in the set of data correspond respectively to x-axis and y-axis spatial coordinates and wherein identifying first or second values for at least some of the test samples in the set of data identifies x- or y-axis coordinates for the test samples that are within a predetermined stringency amount of x- or y-axis coordinates of the control sample.

19. A computer-readable medium for storing computer readable instructions, the instructions being capable of programming a computer to perform a method, the method comprising:
    receiving a set of data produced from testing a set of biological samples, wherein the biological samples include test samples and at least one control sample related to at least some of the test samples by space, time or frequency, wherein the set of data includes first and second values and a quantitative value for each test sample;
    identifying first or second values corresponding to the control sample in the set of data;
    identifying first or second values for at least some of the test samples in the set of data based on the identified first or second values of the control sample and the spatial, temporal or frequency relationship between the control sample and the at least some of the test samples;
    filtering the quantitative values for the at least some of the test samples in the set of data based on the identified first or second values; and
    analyzing the filtered quantitative values of a selected one of the test samples by comparing the quantitative value of a first portion of the filtered quantitative values of the selected test sample at a first pair of x-axis and y-axis spatial coordinates with a sum of the quantitative value of the first portion and the quantitative value of a second portion of the filtered quantitative values of the selected test sample at a second pair of x-axis and y-axis spatial coordinates.

20. The computer-readable medium of claim 19 wherein the first and second values in the set of data identify lanes and row numbers, respectively, for spatially distinguishing mitochondrial and extramitochondrial test samples in an electrophoresis gel, wherein the quantitative values include intensity values for test samples, wherein at least one predetermined lane includes a plurality of mitochondrial and extramitochondrial control samples, and wherein identifying first or second values corresponding to the control sample includes receiving input regarding row numbers of the mitochondrial and extramitochondrial control samples for the set of data, and wherein identifying first or second values for at least some of the test samples includes identifying row numbers based on a preselected lane number for the mitochondrial and extramitochondrial test samples.

21. The computer-readable medium of claim 19 wherein receiving includes receiving the set of data from a DNA sequencer that analyzes an electrophoresis gel having lanes and rows of mitochondrial and extramitochondrial samples, and wherein the first, second and quantitative values in the set of data correspond respectively to lanes, scan numbers and intensity values for each test sample.

22. The computer-readable medium of claim 19 wherein the first and second values correspond respectively to lanes and scan numbers of an electrophoresis gel.

23. The computer-readable medium of claim 19 wherein the first and second values correspond respectively to x-axis and y-axis spatial coordinates.

24. The computer-readable medium of claim 19 wherein analyzing the filtered quantitative values includes determining a percent mitochondrial load of the biological samples based on the filtered quantitative values.

25. The computer-readable medium of claim 19 wherein the first and second values correspond respectively to lanes and scan numbers of an electrophoresis gel, and wherein the method includes providing a slope correction when filtering the quantitative values.

26. The computer-readable medium of claim 19 wherein the first and second values in the set of data correspond to lanes and scan numbers of an electrophoresis gel, and wherein the method includes:
    identifying a lane for the test samples in the set of data based on determined lane and scan numbers of the control sample; and,
    identifying scan numbers for the test samples that are within a predetermined stringency amount of the scan number of the control sample.

27. The computer-readable medium of claim 19 wherein the first and second values in the set of data correspond respectively to x-axis and y-axis spatial coordinates and wherein identifying first or second values for at least some of the test samples in the set of data includes identifying x- or y-axis coordinates for the test samples that are within a predetermined amount of the x- or y-axis coordinates of the control sample.

28. A method for displaying to a user information from biological samples, comprising:
    receiving a set of data produced from testing a set of biological samples, wherein the biological samples include test samples and at least one control sample related to at least some of the test samples by space, time or frequency, and wherein the set of data includes first and second values and a quantitative value for each test sample;
    identifying first or second values corresponding to the control sample in the set of data;
    identifying first or second values for at least some of the test samples in the set of data based on the identified first or second values of the control sample and the spatial, temporal or frequency relationship between the control sample and the at least some of the test samples;
    filtering the quantitative values for the at least some of the test samples in the set of data based on the identified first or second values;
    analyzing each of the test samples by calculating a ratio of a quantitative value of a first component of the first or second value for each test sample to the sum of the quantitative value of the first component and a quantitative value of a second component of the first or second value for each respective test sample; and displaying the filtered quantitative values, so that only quantitative values for test samples of interest are displayed.

29. The method of claim 28 wherein the identifying of the first or second values for at least some of the test samples includes receiving an indication from the user of the spatial, temporal or frequency relationship to be used for the identifying.

30. The method of claim 28 wherein the filtering of the quantitative values for the at least some of the test samples includes receiving an indication from the user of a slope correction for the quantitative values of the test samples.

31. The method of claim 28 wherein the first and second values in the set of data correspond respectively to lanes and scan numbers from an electrophoresis gel, and wherein the filtering of the quantitative values for the at least some of the test samples includes receiving an indication from the user of a stringency amount for the scan numbers of the test samples.

32. A method for generating information based on biological samples, comprising:

receiving a set of data produced from testing a set of biological samples, wherein the biological samples includes a test sample;

filtering the test sample to separate the test sample into at least first and second components;

analyzing the test sample by calculating a ratio of the quantitative value of the first component to the quantitative value of a sum of the first and second components; and displaying results of the analysis.

33. The method of claim 32 wherein the first component is extramitochondrial DNA and the second component is mitochondrial DNA.

34. The method of claim 32 wherein the first component is a first type of mitochondrial DNA and the second component is a second type of mitochondrial DNA.

35. The method of claim 32 wherein the set of data produced from testing a set of biological samples includes at least one control sample, the method further comprising:

filtering the control sample in conjunction with filtering the test sample wherein the control sample is related to the first or second components of the test sample by space, time or frequency; and identifying the first or second components related to the control sample in the set of data, whereby the analysis is performed on a selected one of the first and second identified components.

* * * * *

UNITED STATES PATENT AND TRADEMARK OFFICE
CERTIFICATE OF CORRECTION

PATENT NO. : 6,203,990 B1
DATED : March 20, 2001
INVENTOR(S) : Eoin David Fahy

It is certified that error appears in the above-identified patent and that said Letters Patent is hereby corrected as shown below:

Title page,
Item [56], References Cited, should be included to read as --

| 5,061,067 | 10/1991 | Yamamoto et al. | 356/344 |
| 5,205,917 | 4/1993 | Klock, Jr. | 204/182.8 |
| 5,693,463 | 12/1997 | Edward et al. | 435/6 --. |

Column 21, claim 2,
Line 29, "an as say computer" should read -- an assay computer --.

Column 21, claim 7,
Line 65, "The system of claim wherein" should read
-- The system of claim 1 wherein --.

Signed and Sealed this

Sixteenth Day of October, 2001

Attest:

NICHOLAS P. GODICI
Attesting Officer
Acting Director of the United States Patent and Trademark Office

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Primer extension based on human mitochondrial
      gene encoding cytochrome c oxidase subunit 2

<400> SEQUENCE: 1
tcccctatca tagaagagct tatca                                          25

<210> SEQ ID NO 2
<211> LENGTH: 21
<212> TYPE: DNA
<213> ORGANISM: Artificial Sequence
<220> FEATURE:
<223> OTHER INFORMATION: Primer extension based on human mitochondrial
      gene encoding cytochrome c oxidase subunit 2

<400> SEQUENCE: 2
ggccaattga tttgatggta a                                              21

<210> SEQ ID NO 3
<211> LENGTH: 30
<212> TYPE: DNA
<213> ORGANISM: Artificial Sequence
<220> FEATURE:
<223> OTHER INFORMATION: Primer extension based on human mitochondrial
      gene encoding cytochrome c oxidase subunit 2

<400> SEQUENCE: 3
atgtaattat tatacgaatg ggggcttcaa                                     30
```